United States Patent
Al-Jilaihawi

(10) Patent No.: US 12,226,310 B2
(45) Date of Patent: Feb. 18, 2025

(54) DEVICES, SYSTEMS, AND METHODS TO OPTIMIZE ANNULAR ORIENTATION OF TRANSCATHETER VALVES

(71) Applicant: CEDARS-SINAI MEDICAL CENTER, Los Angeles, CA (US)

(72) Inventor: Hasanian Al-Jilaihawi, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 675 days.

(21) Appl. No.: 16/953,773

(22) Filed: Nov. 20, 2020

(65) Prior Publication Data

US 2021/0093448 A1    Apr. 1, 2021

Related U.S. Application Data

(63) Continuation of application No. 15/554,691, filed as application No. PCT/US2016/021866 on Mar. 10, 2016, now Pat. No. 10,869,756.

(60) Provisional application No. 62/132,161, filed on Mar. 12, 2015.

(51) Int. Cl.
*A61F 2/24* (2006.01)

(52) U.S. Cl.
CPC .......... *A61F 2/2409* (2013.01); *A61F 2/2433* (2013.01); *A61F 2/2436* (2013.01)

(58) Field of Classification Search
CPC .... A61F 2/2409; A61F 2/2433; A61F 2/2436; A61F 2210/0014; A61F 2230/0065; A61F 2250/0003; A61F 2250/007; A61F 2250/006; A61F 2/2418

USPC .......................................................... 623/1.25
See application file for complete search history.

(56) References Cited

U.S. PATENT DOCUMENTS

| | | | |
|---|---|---|---|
| 4,694,838 A | 9/1987 | Wijayarthna et al. | |
| 4,738,667 A | 4/1988 | Galloway | |
| 5,423,829 A | 6/1995 | Pham et al. | |
| 5,833,632 A | 11/1998 | Jacobsen et al. | |
| 5,964,744 A | 10/1999 | Balbierz et al. | |
| 5,964,797 A | 10/1999 | Ho | |
| 5,972,019 A | 10/1999 | Engelson et al. | |
| 6,059,779 A | 5/2000 | Mills | |
| 6,086,557 A | 7/2000 | Morejohn et al. | |
| 6,168,614 B1 * | 1/2001 | Andersen | A61F 2/2433 623/2.15 |

(Continued)

FOREIGN PATENT DOCUMENTS

| | | |
|---|---|---|
| CN | 1106647 A | 8/1995 |
| CN | 1647777 A | 8/2005 |

(Continued)

OTHER PUBLICATIONS

PCT/US2014/060526 International Search Report and Written Opinion dated Feb. 10, 2015; 7 pages.

(Continued)

*Primary Examiner* — Julian W Woo
(74) *Attorney, Agent, or Firm* — NIXON PEABODY LLP

(57) ABSTRACT

In various embodiments, provided herein are methods, devices and systems to optimize annular orientation of transcatheter valves and thereby facilitate transcatheter aortic valve replacement in the setting of challenging cardiovascular anatomy. These methods, devices and systems are used to treat patients with valvular diseases.

24 Claims, 16 Drawing Sheets

(56) References Cited

U.S. PATENT DOCUMENTS

| | | | |
|---|---|---|---|
| 6,217,611 B1 | 4/2001 | Klostermeyer | |
| 6,287,277 B1 | 9/2001 | Yan | |
| 6,350,282 B1 | 2/2002 | Eberhardt | |
| 6,475,232 B1 * | 11/2002 | Babbs | A61F 2/91 |
| | | | 623/1.13 |
| 6,589,230 B2 | 7/2003 | Gia et al. | |
| 6,949,119 B2 * | 9/2005 | Myers | A61L 31/10 |
| | | | 623/1.13 |
| 6,953,473 B2 | 10/2005 | Porter | |
| 6,964,657 B2 | 11/2005 | Cragg et al. | |
| 6,976,965 B2 | 12/2005 | Corl et al. | |
| 7,134,994 B2 | 11/2006 | Alpert et al. | |
| 7,150,758 B2 * | 12/2006 | Kari | A61F 2/06 |
| | | | 623/1.25 |
| 7,340,288 B1 | 3/2008 | Karicherla et al. | |
| 7,534,259 B2 * | 5/2009 | Lashinski | A61F 2/2439 |
| | | | 623/2.1 |
| 7,935,144 B2 | 5/2011 | Robin et al. | |
| 8,070,800 B2 | 12/2011 | Lock et al. | |
| 8,092,524 B2 | 1/2012 | Nugent et al. | |
| 8,372,069 B2 | 2/2013 | Kassab | |
| 8,377,112 B2 | 2/2013 | Griffin et al. | |
| 8,408,214 B2 | 4/2013 | Spenser | |
| 8,430,927 B2 | 4/2013 | Bonhoeffer | |
| 8,491,648 B2 | 7/2013 | Hassan et al. | |
| 8,568,477 B2 * | 10/2013 | Lashinski | A61F 2/2409 |
| | | | 623/2.38 |
| 8,801,768 B2 * | 8/2014 | Karwa | A61B 17/12118 |
| | | | 623/1.11 |
| 9,095,434 B2 * | 8/2015 | Rowe | A61F 2/2433 |
| 9,427,316 B2 * | 8/2016 | Schweich, Jr. | A61F 2/2445 |
| 2002/0169474 A1 | 11/2002 | Kusleika et al. | |
| 2004/0073141 A1 | 4/2004 | Hartley et al. | |
| 2004/0172081 A1 | 9/2004 | Wang | |
| 2005/0203425 A1 | 9/2005 | Langston | |
| 2005/0240200 A1 | 10/2005 | Bergheim | |
| 2005/0256566 A1 | 11/2005 | Gabbay | |
| 2005/0267010 A1 | 12/2005 | Goodson et al. | |
| 2006/0064114 A1 | 3/2006 | Obitsu et al. | |
| 2006/0155305 A1 | 7/2006 | Freudenthal | |
| 2006/0287719 A1 | 12/2006 | Rowe et al. | |
| 2007/0050021 A1 | 3/2007 | Johnson | |
| 2007/0203562 A1 | 8/2007 | Malewicz et al. | |
| 2008/0027334 A1 | 1/2008 | Langston | |
| 2008/0033467 A1 | 2/2008 | Miyamoto et al. | |
| 2008/0183273 A1 | 7/2008 | Mesana et al. | |
| 2008/0221551 A1 | 9/2008 | Goodson et al. | |
| 2008/0306499 A1 | 12/2008 | Katoh et al. | |
| 2008/0319541 A1 | 12/2008 | Filsoufi | |
| 2009/0082678 A1 | 3/2009 | Smith | |
| 2009/0248143 A1 | 10/2009 | Laham | |
| 2009/0259292 A1 | 10/2009 | Bonhoeffer | |
| 2009/0276040 A1 | 11/2009 | Rowe et al. | |
| 2010/0030330 A1 | 2/2010 | Bobo et al. | |
| 2010/0076549 A1 | 3/2010 | Keidar et al. | |
| 2010/0094209 A1 | 4/2010 | Drasler et al. | |
| 2010/0168840 A1 | 7/2010 | Kassab | |
| 2010/0185275 A1 | 7/2010 | Richter et al. | |
| 2010/0191272 A1 | 7/2010 | Keating | |
| 2010/0211094 A1 | 8/2010 | Sargent | |
| 2010/0331948 A1 | 12/2010 | Turovskiy et al. | |
| 2011/0098802 A1 * | 4/2011 | Braido | A61F 2/2466 |
| | | | 623/2.11 |
| 2011/0137397 A1 | 6/2011 | Chau et al. | |
| 2012/0059458 A1 | 3/2012 | Buchbinder et al. | |
| 2012/0130230 A1 | 5/2012 | Eichler et al. | |
| 2012/0158129 A1 | 6/2012 | Duffy et al. | |
| 2012/0283757 A1 | 11/2012 | Miller et al. | |
| 2012/0283812 A1 | 11/2012 | Lagodzki et al. | |
| 2012/0283820 A1 | 11/2012 | Tseng et al. | |
| 2012/0310328 A1 | 12/2012 | Olson et al. | |
| 2012/0310330 A1 | 12/2012 | Buchbinder et al. | |
| 2013/0090726 A1 | 4/2013 | Rowe et al. | |
| 2013/0109960 A1 | 5/2013 | Stinis | |
| 2013/0116779 A1 | 5/2013 | Weber | |
| 2013/0166017 A1 | 6/2013 | Cartledge et al. | |
| 2013/0190857 A1 | 7/2013 | Mitra et al. | |
| 2013/0190865 A1 | 7/2013 | Anderson | |
| 2013/0211509 A1 | 8/2013 | Spenser | |
| 2013/0261738 A1 | 10/2013 | Clague et al. | |
| 2013/0261739 A1 | 10/2013 | Kuehn | |
| 2013/0274618 A1 | 10/2013 | Hou et al. | |
| 2013/0331864 A1 | 12/2013 | Jelich et al. | |
| 2013/0331921 A1 | 12/2013 | Roubin | |
| 2014/0114402 A1 | 4/2014 | Ahlberg et al. | |
| 2014/0135799 A1 | 5/2014 | Henderson | |
| 2014/0171958 A1 | 6/2014 | Baig | |
| 2014/0194981 A1 | 7/2014 | Menk et al. | |
| 2014/0200662 A1 | 7/2014 | Eftel et al. | |
| 2014/0222144 A1 | 8/2014 | Eberhardt et al. | |
| 2014/0236287 A1 | 8/2014 | Clague et al. | |
| 2014/0243966 A1 | 8/2014 | Garde et al. | |
| 2014/0277419 A1 | 9/2014 | Garde et al. | |
| 2014/0303719 A1 | 10/2014 | Cox et al. | |
| 2014/0350669 A1 | 11/2014 | Gillespie et al. | |
| 2016/0206424 A1 | 7/2016 | Al-Jilaihawi | |
| 2016/0228013 A1 | 8/2016 | Al-Jilaihawi et al. | |
| 2016/0228241 A1 | 8/2016 | Al-Jilaihawi | |
| 2016/0235422 A1 | 8/2016 | Al-Jilaihawi et al. | |
| 2016/0302920 A1 | 10/2016 | Al-Jilaihawi | |
| 2016/0310699 A1 | 10/2016 | Al-Jilaihawi | |
| 2018/0078363 A1 | 3/2018 | Al-Jilaihawi | |

FOREIGN PATENT DOCUMENTS

| | | |
|---|---|---|
| CN | 101474102 A | 7/2009 |
| CN | 101489504 A | 7/2009 |
| CN | 101947146 A | 1/2011 |
| CN | 101972177 A | 2/2011 |
| CN | 103237523 A | 8/2013 |
| CN | 104220028 A | 12/2014 |
| CN | 104334119 A | 2/2015 |
| CN | 105611871 A | 5/2016 |
| CN | 105611889 A | 5/2016 |
| CN | 105744969 A | 7/2016 |
| CN | 105764447 A | 7/2016 |
| CN | 107405191 A | 11/2017 |
| EP | 2732796 A1 | 5/2014 |
| EP | 3054838 A1 | 8/2016 |
| EP | 3057522 A1 | 8/2016 |
| EP | 3079633 A1 | 10/2016 |
| EP | 3099345 A1 | 12/2016 |
| EP | 3267940 A1 | 1/2018 |
| WO | 1996017644 A1 | 6/1996 |
| WO | WO1998048879 | 11/1998 |
| WO | WO1999/15223 A1 | 4/1999 |
| WO | WO1999/15227 A1 | 4/1999 |
| WO | WO20020249511 | 6/2002 |
| WO | WO2005059379 A1 | 6/2005 |
| WO | WO2007081820 A1 | 7/2007 |
| WO | WO2010085659 A1 | 7/2010 |
| WO | WO2011039091 A1 | 4/2011 |
| WO | WO2012009675 A2 | 1/2012 |
| WO | WO2012161769 A1 | 11/2012 |
| WO | WO2012/173697 A1 | 12/2012 |
| WO | WO2013061281 A1 | 5/2013 |
| WO | WO2014145469 A1 | 9/2014 |
| WO | WO2015/054296 A1 | 4/2015 |
| WO | WO2015/057735 A1 | 4/2015 |
| WO | WO2015/057995 A2 | 4/2015 |
| WO | WO2015/058001 A1 | 4/2015 |
| WO | WO2015/089334 A1 | 6/2015 |
| WO | WO2015/117025 A1 | 8/2015 |
| WO | WO2016145250 A1 | 9/2016 |

OTHER PUBLICATIONS

PCT/US2014/060957 International Search Report and Written Opinion dated Apr. 1, 2015; 10 pages.

PCT/US2014/060966 International Search Report and Written Opinion dated Jan. 29, 2015; 6 pages.

(56) References Cited

OTHER PUBLICATIONS

PCT/US2014/059547 International Search Report and Written Opinion dated Mar. 3, 2015; 9 pages.
PCT/US2014/069849 International Search Report and Written Opinion dated Mar. 2, 2015; 8 pages.
PCT/US2015/013956 International Search Report and Written Opinion dated Jun. 26, 2015; 10 pages.
Astarci et al. Transapical explantation of an embolized transcatheter valve. Interact Cardiovasc Thorac Surg (2011). 13:1-2.
Blows et al. The pressure wire in practice. Heart (2007). 93:419-422.
Bonhoeffer et al. The multi-track angiography catheter: a new tool for complex catheterisation in congenital heart disease. Heart (1996). 76:173-177.
Chiam et al. Percutaneous Transcatheter Mitral Valve Repair. J Am Coll Cardiol (2011). 4(1):1-13.
Ho, S.Y. Structure and anatomy of the aortic root. Eur J Echocardiogr (2009). 10:i3-i10.
Jolicoeur et al. Tiara: A Novel Catheter-Based Mitral Valve Bioprosthesis Initial Experiments and Short-Term Pre-Clinical Results. J Am Coll Cardiol (2012). 60(15):1430-1431.
Lange et al. Diagnostic Cardiac Catheterization. Circulation (2003). 107:e111-e113.
Masson et al. Percutaneous Treatment of Mitral Regurgitation. Circ Cardiovasc Interv (2009). 2:140-146.
McCarthy et al. Anatomy of the mitral valve: understanding the mitral valve complex in mitral regurgitation. Eur J Echocardiogr (2010). 11:i3-i9.
Ormiston et al. Bioabsorbable Coronary Stents (2009). Circ Cardiovasc Interv (2009). 2:255-260.
Sievers et al. The everyday used nomenclature of the aortic root components: the tower of Babel? Eur J Cardio-Thorac Surg (2011). 0:1-5.
Sinning et al. Aortic Regurgitation Index Defines Severity of Peri-Prosthetic Regurgitation and Predicts Outcome in Patients After Transcatheter Aortic Valve Implantation. J Am Coll Cardiol (2012). 59(13):1134-1141.
Tonino et al. Fractional Flow Reserve versus Angiography for Guiding Percutaneous Coronary Intervention. New Engl J Med (2009). 360(3):213-224.
Tsai et al. Transcatheter Retrieval of Dislodged Port-A Catheter Fragments: Experience with 47 Cases. Acta Cardiol Sin (2006). 22:221-228.
Van Mieghem et al. Anatomy of the Mitral Valvular Complex and Its Implications for Transcatheter Interventions for Mitral Regurgitation. J Am Coll Cardiol (2010). 56(8):617-626.
PCT/US2014/060526 International Preliminary Report on Patentability dated Apr. 19, 2016, 7 pages.
PCT/US2014/060957 International Preliminary Report on Patentability dated Apr. 19, 2016, 10 pages.
PCT/US2014/060966 International Preliminary Report on Patentability dated Apr. 19, 2016, 6 pages.
Extended European Search Report for EP Application No. 14853895.2 dated May 10, 2017, 8 pages.
Partial Supplementary European Search Report for EP Application No. 14851950.7 dated Apr. 10, 2017, 6 pages.
Extended European Search Report for EP Application No. 14869869.9 dated May 4, 2017, 7 pages.
PCT/US2016/021866 International Search Report and Written Opinion dated May 23, 2016, 11 pages.
PCT/US2016/021866 International Preliminary Report on Patentability dated Sep. 21, 2017, 9 pages.
EP16762555.7 Supplementary European Search Report dated Oct. 5, 2018, 8 pages.
Crushing. (n.d.) American Heritage Dictionary of the English Language, Fifth Edition, 2011, retrieved from https://thefreedictionary.com/crushing.
Compress. (n.d.) Merriam-Webster, 2018, retrieved from https://www.merriam-webster.com/dictionary/compressr.
EP 14869869.9 Examination Report dated Jan. 23, 2019, 4 pages.
PCT/US2014/069849 International Preliminary Report on Patentability dated Jun. 14, 2016, 7 pages.
PCT/US2014/059547 International Preliminary Report on Patentability dated Apr. 12, 2016, 7 pages.
EP 14851950.7 Examination Report dated May 24, 2018, 4 pages.
EP 14851950.7 Extended European Search Report dated Jul. 12, 2017, 10 pages.
EP 15743048.9 Extended Search Report dated Aug. 24, 2017, 8 pages.
CN Search Report issued Feb. 20, 2023 for 202010663940.4, 8 pages.

* cited by examiner

DEVICES, SYSTEMS, AND METHODS TO OPTIMIZE ANNULAR ORIENTATION OF TRANSCATHETER VALVES

CROSS-REFERENCE TO RELATED APPLICATIONS

This application claims the benefit of priority under 35 U.S.C. § 120 as a continuation of U.S. application Ser. No. 15/554,691, filed Aug. 30, 2017, which is the National Phase of International Application No. PCT/US2016/021866, filed Mar. 10, 2016, which designated the U.S. and that International Application was published under PCT Article 21(2) in English, which also includes a claim of priority under 35 U.S.C. § 119 (e) to U.S. provisional patent application No. 62/132,161 filed Mar. 12, 2015, the entirety of which is hereby incorporated by reference.

FIELD OF INVENTION

This invention relates to devices, systems, and methods to optimize annular orientation of transcatheter valves, which may be used to treat valvular heart diseases.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Valvular heart disease is characterized by damage to or a defect in one of the four heart valves: the mitral, aortic, tricuspid or pulmonary. The mitral and tricuspid valves control the flow of blood between the atria and the ventricles (the upper and lower chambers of the heart). The pulmonary valve controls the blood flow from the heart to the lungs, and the aortic valve governs blood flow between the heart and the aorta, and thereby to the blood vessels in the rest of the body. The mitral and aortic valves are most frequently affected by valvular heart disease.

Normally functioning valves ensure that blood flows with proper force in the proper direction at the proper time. In a valvular heart disease, a heart valve becomes too narrow and hardened (stenotic) to open fully, or is unable to close completely (incompetent). A stenotic valve forces blood to back up in the adjacent heart chamber, while an incompetent valve allows blood to leak back into the chamber it previously exited. To compensate for poor pumping action, the heart muscle enlarges and thickens, thereby losing elasticity and efficiency. In addition, in some cases, blood pooling in the chambers of the heart has a greater tendency to clot, increasing the risk of stroke or pulmonary embolism. The severity of valvular heart disease varies. In mild cases there may be no symptoms, while in advanced cases, valvular heart disease may lead to congestive heart failure and other complications. Treatment depends upon the extent of the disease.

Transcatheter valve therapies are one treatment option for patients. For example, transcatheter aortic valve replacement (TAVR—also known as TAVI or transcatheter aortic valve implantation) is a procedure for patients with severe symptomatic aortic stenosis (narrowing of the aortic valve opening) who are not candidates for traditional open chest surgery or are high-risk operable candidates. In these procedures, a replacement valve is inserted percutaneously using a catheter and implanted in the orifice of the native aortic valve. Replacement valves may be artificial (prosthetic valves) or made from animal tissue (bioprosthetic valves). Diseased mitral, tricuspid or pulmonary valves may also be treated with transcatheter valve replacement or implantation. The type of replacement valve selected depends on the patient's age, condition, and the specific valve affected.

Since transcatheter valves, unlike surgical valves, are not sewn into the heart, they require a landing zone to which their external profiles must conform and anchor to. Also, some degree of stenosis in the native valve is generally necessary to provide a consistently stable anchor point. However, the native valve's shape, size and stenosis vary considerably, and hence are not always favorable, suitable or safe for the deployment of transcatheter valves. If an implanted transcatheter valve does not conform to the native valve's anatomy or is not stably anchored, paravalvular leakage as well as device embolization or malposition may occur. To fill the gaps between the transcatheter valve and the native valve's anatomical structures, an external cuff (either fabric or hydrogel) may be added, but this cannot correct large differences in dimension.

SUMMARY OF THE INVENTION

To solve these problems, described herein is a Device to Optimize aNnUlar orientation of Transcatheter valves (DONUT). DONUT can correct large differences between a native valve's anatomical dimensions and the external dimensions of a transcatheter valve stent frame. DONUT may act as a mould for the anatomy of a native valve externally, and its central hole may match a transcatheter replacement valve, for example, a standardized valve or those commercially available ones including but not limited to the MEDTRONIC COREVALVE device and the EDWARDS SAPIEN device. The outside perimeter of the DONUT conforms to the anatomy of a native valve, cardiovascular structure or chamber, and its center hole fits a transcatheter valve. Also described herein is a method of using DONUT for transcatheter heart valve implantation. DONUT is first deployed to a diseased heart valve (e.g., the aortic valve and mitral valve) and serves as a consistent landing zone and stable anchor point. Next, a transcatheter valve is implanted into the center hole of DONUT, even when the native valve's anatomy and stenosis are not favorable, suitable or safe for the direct deployment of a transcatheter valve.

The following embodiments and aspects thereof are described and illustrated in conjunction with devices, systems, and methods, which are meant to be exemplary and illustrative, not limiting in scope.

Provided herein are various embodiments of a device for a transcatheter valve replacement or implantation. The device may consist of, may consist essentially of, or may comprise a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive a replacement heart valve and the periphery is configured to conform to the anatomy of a native heart valve peri-annular region, cardiovascular structure or chamber, herein also described as the "landing zone".

In various embodiments, provided herein is a device for a transcatheter valve replacement or implantation. In some embodiments, the device may consist of, may consist essentially of, or may comprise a replacement heart valve and a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive the replacement heart valve and the periphery is configured to conform to the anatomy of a native heart valve, cardiovascular structure or chamber.

In some embodiments, the device may consist of, may consist essentially of, or may comprise a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive a replacement heart valve and the periphery is configured to conform to the anatomy of a native heart valve peri-annular region, cardiovascular structure or chamber; and a first delivery catheter, wherein the first delivery catheter is configured to deploy the ring-shaped article into the native heart valve peri-annular region.

In some embodiments, the device may consist of, may consist essentially of, or may comprise a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive a replacement heart valve and the periphery is configured to conform to the anatomy of a native heart valve peri-annular region, cardiovascular structure or chamber; and a second delivery catheter, wherein the second delivery catheter is configured to deploy the replacement heart valve into the center hole of the ring-shaped article.

In various embodiments, the device described herein further comprises a guide wire, wherein a delivery catheter can be inserted over the guide wire. In various embodiments, the native heart valve may be a mitral, aortic, tricuspid or pulmonary valve.

Provided are various embodiments of a method for transcatheter valve replacement or implantation. In accordance with the present invention, the method may be used to treat a subject with valvular diseases. In some embodiments, the method may consist of, may consist essentially, or may comprise the following steps: providing a device as described herein, deploying the device to a native heart valve peri-annular region; providing a replacement heart valve; and deploying the replacement heart valve into the center hole of the device. In various embodiments, the device and the replacement valve are deployed individually. In certain embodiments, the device is deployed before the replacement valve is deployed.

BRIEF DESCRIPTION OF FIGURES

Exemplary embodiments are illustrated in the referenced figures. It is intended that the embodiments and figures disclosed herein are to be considered illustrative rather than restrictive.

FIG. 5 depicts, in accordance with various embodiments of the present invention, one non-limiting example of DONUT in its expanded status.

DETAILED DESCRIPTION OF THE INVENTION

Figure 1A:
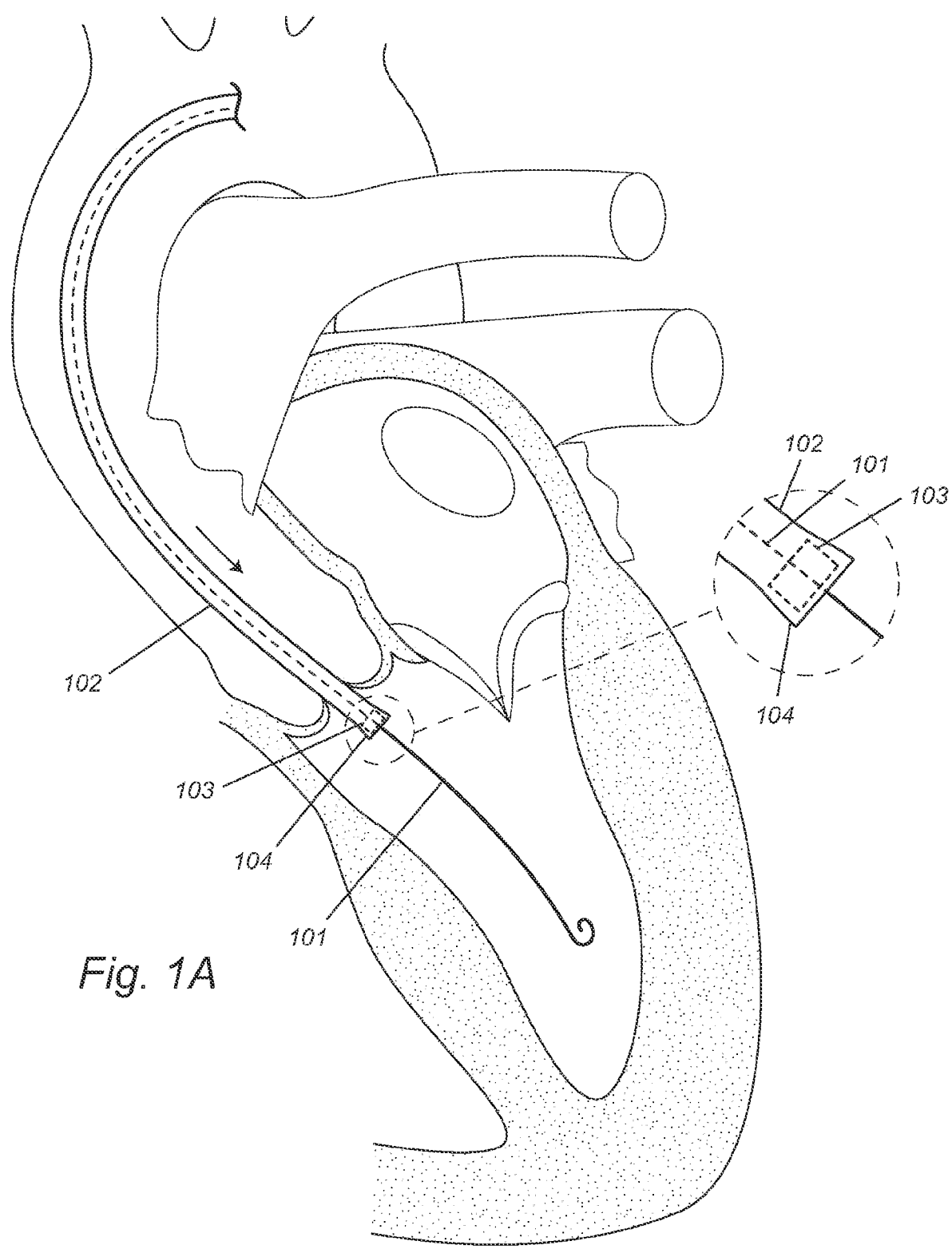
FIGS. 1A-B depict, in accordance with various embodiments of the present invention, a self-expandable DONUT device and a transfemoral procedure of deploying the DONUT device to the aortic valve. 101 refers to a guide wire; 102 refers to a first delivery catheter; 103 refers to a self-expandable DONUT device; and 104 refers to an enclosing sheath at the first delivery catheter's distal end.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Devices and Systems

Provided herein are various embodiments of a device for a transcatheter valve replacement or implantation. In some embodiments, the device may consist of, may consist essentially of, or may comprise a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive a replacement heart valve and the periphery is configured to conform to the anatomy of a native heart valve peri-annular region, cardiovascular structure or chamber. In various embodiments, the native heart valve may be a mitral, aortic, tricuspid or pulmonary valve. In certain embodiments, the device further comprises the replacement heart valve.

In various embodiments, the device further comprises a first delivery catheter, wherein the first delivery catheter is configured to deploy the ring-shaped article into the native heart valve peri-annular region.

In accordance with the present invention, the first delivery catheter can be comprised of one or more components. In some embodiments, the first delivery catheter comprises an inflatable balloon near or at its distal end, wherein the compressed ring-shaped article is configured to be mounted on the inflatable balloon, and wherein the inflatable balloon is configured to be inflated so as to expand the compressed ring-shaped article. In other embodiments, the first delivery catheter comprises an enclosing sheath near or at its distal end, wherein the compressed ring-shaped article is configured to be enclosed in the enclosing sheath, and wherein the enclosing sheathe is configured to be retracted so as to expand the compressed ring-shaped article. In various embodiments, the enclosing sheath is just the distal portion of the first delivery catheter. In various embodiments, the enclosing sheath is a separate component located near or at the distal end of the first delivery catheter.

In various embodiments, the device further comprise a second delivery catheter, wherein the second delivery catheter is configured to deploy the replacement heart valve into the center hole of the ring-shaped article.

In some embodiments, the first delivery catheter and the second delivery catheter are the same delivery catheter. In other embodiments, the first delivery catheter and the second delivery catheter are two different delivery catheters.

In various embodiments, provided herein is a device for a transcatheter valve replacement or implantation. In some embodiments, the device may consist of, may consist essentially of, or may comprise a replacement heart valve and a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive the replacement heart valve and the periphery is configured to conform to the anatomy of a native heart valve peri-annular region, cardiovascular structure or chamber.

In some embodiments, the device may consist of, may consist essentially of, or may comprise a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive a replacement heart valve and the periphery is configured to conform to the anatomy of a native heart valve peri-annular region, cardiovascular structure or chamber; and a first delivery catheter, wherein the first delivery catheter is configured to deploy the ring-shaped article into the native heart valve peri-annular region.

In some embodiments, the device may consist of, may consist essentially of, or may comprise a ring-shaped article, wherein the ring-shaped article comprises an outside surface, wherein the outside surface comprises an inward surface area that faces toward the center of the ring-shaped article and forms a center hole, wherein the outside surface comprises an outward surface area that faces away from the center of the ring-shaped article and forms a periphery, wherein the ring-shaped article has a compressed status and an expanded status, and wherein when the ring-shaped article is expanded, the center hole is configured to receive a replacement heart valve and the periphery is configured to conform to the anatomy of a native heart valve peri-annular region, cardiovascular structure or chamber; and a second delivery catheter, wherein the second delivery catheter is configured to deploy the replacement heart valve into the center hole of the ring-shaped article.

In various embodiments, the device further comprises a guide wire. In one embodiment, the first delivery catheter is configured to be inserted over the guide wire. In another embodiment, the second delivery catheter is configured to be inserted over the guide wire.

In various embodiments, the periphery of the ring-shaped article is configured to anchor to the native heart valve peri-annular region. In one embodiment, the periphery is configured to anchor to the ventricular side of the native heart valve. In another embodiment, the periphery is configured to anchor to the atrial side of the native heart valve. Still in another embodiment, the periphery is configured to anchor to the aorta or arterial side of the native heart valve. Still in another embodiment, the periphery is configured to anchor to another cardiovascular structure or chamber, including but not restricted to the right atrial surface, the superior vena cava, the inferior vena cava or the pulmonary artery.

In various embodiments, the periphery is configured to anchor onto the annulus of the native valve or valve annulus. In various embodiments, the periphery is configured to anchor onto the ventricular wall near the valve annulus. In various embodiments, the periphery is configured to anchor onto the atrial wall near the valve annulus. In various embodiments, the periphery is configured to anchor onto the aortic wall near the valve annulus. In various embodiments, the periphery is configured to anchor the arterial wall near the valve annulus. In some embodiments, the periphery is configured to anchor not onto the valve annulus but onto the ventricular wall, the atrial wall, the aortic wall, or the arterial wall near the valve annulus. In other embodiments, the periphery is configured to anchor onto the valve annulus and onto the ventricular wall, the atrial wall, the aortic wall, or the arterial wall near the valve annulus. In some embodiments, the anchored periphery pushes the native leaflets aside. In other embodiments, the anchored periphery does not push the native leaflets aside.

In various embodiments, the ring-shaped article is about 5-55 mm in height. In various embodiments, the center hole of the ring-shaped article is about 10-55 mm in diameter. In various embodiments, the periphery of the ring-shaped article is about 15-80 mm in diameter. In some embodiments, the "diameter" used herein refers to the periphery's diameter (i.e., peripheral diameter) when the device is expanded. In various embodiments, the periphery of the ring-shaped article has an adjustable diameter. A user may measure the native valve's dimensions, adjust the periphery's diameter to fit the size and shape of the native valve, compress and load the device to a delivery catheter, deliver and deploy the device to the native valve, to which the periphery of the expanded device conforms and anchors. In one embodiment, the ring-shaped article's height is less than the replacement valve's height. In another embodiment, the ring-shaped article's height is about 5-10%, 10-20%, 20-30%, 30-40%, 40-50%, 50-60%, 60-70%, 70-80%, 80-90%, or 90-95% of the replacement valve's height. In various embodiments, the ring-shaped article does not have a diaphragm.

In various embodiments, the ring-shaped article is shaped as a circular, elliptical, oval, or D ring, or other suitable shapes that conform to a native heart valve peri-annular region. In various embodiments, the periphery is shaped as a circular, elliptical, oval, or D ring, or other suitable shapes that conform to a native heart valve peri-annular region. In various embodiments, the center hole is shaped as a circular, elliptical, oval, or D ring, or other suitable shapes that accommodate a replacement heart valve. In various embodiments, the center hole's shape matches the replacement valve's shape.

In various embodiments, the ring-shaped article is self-expandable or balloon expandable. In various embodiments, the ring-shaped article comprises a stent frame. In some embodiments, the stent frame of the ring-shaped article is made of iron, platinum, titanium, nickel, chromium, cobalt, magnesium, stainless steel, nitinol (nickel-titanium), nickel-chromium, cobalt-chromium, or platinum-iridium, or a combination thereof.

In various embodiments, the ring-shaped article comprises an external layer over the stent frame. In some embodiments, the external layer is made of an animal tissue or a synthetic material, or a combination thereof. Examples of suitable animal tissues include but are not limited to bovine-derived, porcine-derived, equine-derived, human-derived cardiovascular or stem-cell derived tissues. Examples of suitable synthetic materials include but are not limited to polyester fabric, hydrogel, plastic resin, expansile polymer or inflatable hollow plastic material.

In various embodiments, the ring-shaped article comprises entirely a hollow plastic material that may be inflated with air, fluid or a plastic resin.

In various embodiments, the replacement heart valve is configured to anchor to the center hole of the ring-shaped article. In various embodiments, the ring-shaped and the replacement heart valve are separate items and are individually delivered and/or deployed. In certain embodiments, the ring-shaped article is deployed before the replacement heart valve is deployed.

In some embodiments, the ring-shaped article and the replacement heart valve are not connected to each other before, during or after their deployment. In other embodiments, the ring-shaped article and the replacement heart valve are not connected before deployment and are connected after deployment. In various embodiments, the ring-shaped article and the replacement heart valve are connected via a connector including but not limited to a hinge, click-and-lock system, tongue-and-groove system, interlocking structure, clasp, hook, ring, bolts, nut, screw, nail, fastener, magnet, mortise and/or tenon. In some embodiments, the connector comprises two or more components, for example, a click-and-lock system or a tongue-and-groove system. In other embodiments, the connector comprises only one component, for example, a bridge, string, wire, beam or joist.

In various embodiments, the replacement heart valve is about 10-55 mm in height. In various embodiments, the replacement heart valve is about 10-55 mm in diameter.

In various embodiments, the cross section of the replacement valve is a circle, ellipse, oval, or D-shape, or other suitable shapes that accommodate a native heart valve. In various embodiments, the cross section of the replacement valve is a circle, ellipse, oval, or D-shape, or other suitable shapes that accommodate the center hole of the ring-shaped article. In various embodiments, the replacement valve's shape matches with the center hole's shape.

In various embodiments, the replacement heart valve is a self-expandable valve, a balloon expandable valve, or any other suitable replacement valve. A non-limiting example of a self-expandable replacement valve is the MEDTRONIC COREVALVE, which is constructed with a nitinol self-expanding valve stent frame and porcine pericardial leaflets. A non-limiting example of a balloon-expandable replacement valve is the EDWARDS SAPIEN XT VALVE, which is constructed with a cobalt-chromium balloon-expandable valve stent frame and bovine pericardial leaflets.

In various embodiments, the replacement valve comprises a stent frame. In some embodiments, the stent frame of the replacement valve is made of iron, platinum, titanium, nickel, chromium, cobalt, magnesium, stainless steel, nitinol (nickel-titanium), nickel-chromium, cobalt-chromium, or platinum-iridium, or a combination thereof.

In some embodiments, the replacement heart valve is a prosthetic valve, a bioprosthetic valve, or any other suitable replacement valve. In accordance with the present invention, a prosthetic valve is made of purely artificial or non-biological materials, and a bioprosthetic valve is made of animal tissues alone or in combination with artificial or non-biological materials. In various embodiments, the replacement valve comprises one, two, three, or more leaflets. In various embodiments, the leaflets may be biological or artificial.

Suitable examples of guide wires, sheaths, and catheters that may be utilized with the presently disclosed devices, systems and methods described herein will be apparent to a person of skill in the art. Examples of suitable guidewires, sheaths and catheters are disclosed in for example, Ye et al. (Transapical aortic valve implantation in humans. Ye J, Cheung A, Lichtenstein S V, Carere R G, Thompson C R, Pasupati S, Webb J G. J Thorac Cardiovasc Surg. 2006 May; 131(5):1194-6) and Lichtenstein et al. (Transapical transcatheter aortic valve implantation in humans: initial clinical experience. Lichtenstein S V, Cheung A, Ye J, Thompson C R, Carere R G, Pasupati S, Webb J G. Circulation. 2006 Aug. 8; 114 (6):591-6. Epub 2006 Jul. 31), the contents of each of which are herein incorporated by reference.

Materials which may be used to construct the device are well known in the art, for example as described in U.S. Publication No. US2011/0319989, which is incorporated by reference herein in its entirety.

Methods

Provided are various embodiments of a method for transcatheter valve replacement or implantation. In accordance with the present invention, the method may be used to treat a subject with valvular diseases. In some embodiments, the method may consist of, may consist essentially, or may comprise the following steps: providing a device as described herein, deploying the device to a native heart valve peri-annular region; providing a replacement heart valve; and deploying the replacement heart valve into the center hole of the device. In various embodiments, the device and the replacement valve are deployed individually. In certain embodiments, the device is deployed before the replacement valve is deployed.

In various embodiments, the device may be deployed antegradely (i.e., along the blood flow direction) or retrogradely (i.e., against the blood flow direction). In some embodiments, the device is deployed transfemorally, transaortically, transseptally, transapically, or by alternative arterial or venous approach. In some embodiments, the replacement valve is deployed transfemorally, transaortically, transseptally, transapically, or by alternative arterial or venous approach.

In various embodiments, the device and the replacement valve are not connected before, during, after their deployment. In various embodiments, the device and the replacement valve are connected not before but after their deployment.

In various embodiments, deploying the device comprises delivering the compressed device to the native heart valve peri-annular region, expanding the compressed device in the native heart valve peri-annular region and anchoring the expanded device to the native heart valve peri-annular region. In some embodiments, the compressed device is balloon-expandable, and is deployed using a delivery catheter having an inflatable balloon at or near the distal end of the delivery catheter. In other embodiments, the compressed device is self-expandable, and is deployed using a delivery catheter having an enclosing sheath at or near the distal end of the delivery catheter.

In various embodiments, anchoring comprises anchoring the expanded device onto the valve annulus. In various embodiments, anchoring comprises anchoring the expanded device onto the ventricular wall near the valve annulus. In various embodiments, anchoring comprises anchoring the expanded device onto the atrial wall near the valve annulus. In various embodiments, anchoring comprises anchoring the expanded device onto the aortic wall near the valve annulus. In various embodiments, anchoring comprises anchoring the expanded device onto the arterial wall near the valve annulus.

One of the core principles of the invention is that the device should not disrupt the native valve itself so are to prevent hemodynamic compromise. In some examples, the device may be deployed in a cardiovascular structure or chamber distinct from the native valves to act as a platform for deployment of a transcatheter valve. In some examples, this distinct cardiovascular structure or chamber may include but is not restricted to the superior or inferior vena cava, the pulmonary artery or the ascending or descending aorta.

In various embodiments, the subject is a human. In various embodiments, the subject is a mammal. In various embodiments, the devices, systems and methods described herein are configured for humans. One of skill in the art would readily appreciate that the devices, systems and methods described herein could be customized for use in almost any mammal in which a heart valve may be replaced. "Mammal" as used herein refers to any member of the class Mammalia, including but not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult, newborn, fetuses, male or female mammalian heart surgery is within the scope of this disclosure.

Also in accordance with the present invention, as regular TAVR and TMVR are known surgical procedures, one of ordinary skill in the art would readily recognize that the method could involve other additional steps, which are not described in details here. These additional steps include, but are not limited to, anesthesia, sterilization, heparinization, accessing the patient's heart via various routes such as transfemoral, transaortic, transapical, transseptal, transcaval, transaxillary, and transsubclavian approaches, ventricular pacing, stitching of the access site or percutaneous femoral closure. For example, more information on these procedures are described in Masson et al. (Percutaneous treatment of mitral regurgitation; Circ Cardiovasc Interv. 2009 April; 2(2):140-6.) and Chiam et al. (Percutaneous transcatheter mitral valve repair: a classification of the technology; JACC Cardiovasc Interv. 2011 Jan. 4(1):1-13.), each of which is incorporated herein by reference in its entirety.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 Self-Expandable DONUT

For Aortic Valve

Figure 1B:
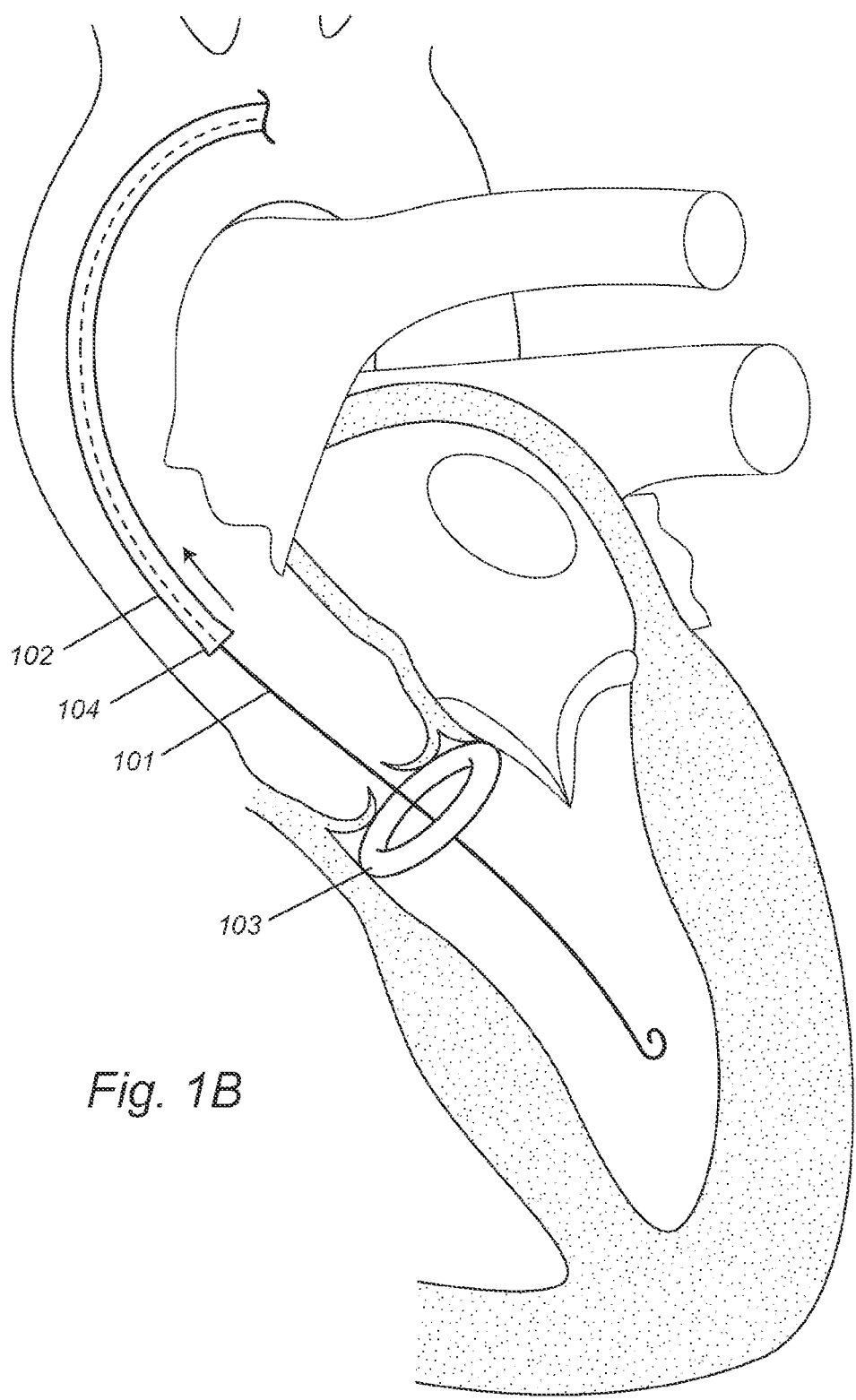

FIGS. 1A-1B illustrate an example of an implantation procedure for a DONUT device as disclosed herein. After induction of anesthesia, and sterile preparation, an incision is performed at the femoral artery. Alternatively, percutaneous femoral access may be performed with or without pre-closure. A guide wire 101 is inserted via the femoral artery and the ascending aorta through the aortic valve into the left ventricle (FIG. 1A). A self-expandable DONUT device 103 is compressed and enclosed in the enclosing sheath 104 at the distal end of a first delivery catheter 102. The loaded first delivery catheter 102 is advanced over the guide wire 101 and inserted through the aortic valve into the left ventricle, and places the compressed DONUT device 103 on the ventricular side of the aortic valve and near the valve annulus (FIG. 1A). The first delivery catheter 102 is retracted and the compressed DONUT device 103 is hence released out of the enclosing sheath 104 to expand (FIG. 1B). The expanded DONUT device's periphery conforms to the aortic valve's peri-annular anatomy and anchors to the ventricular wall near the valve annulus (FIG. 1B).

For Mitral Valve

Figure 1C:
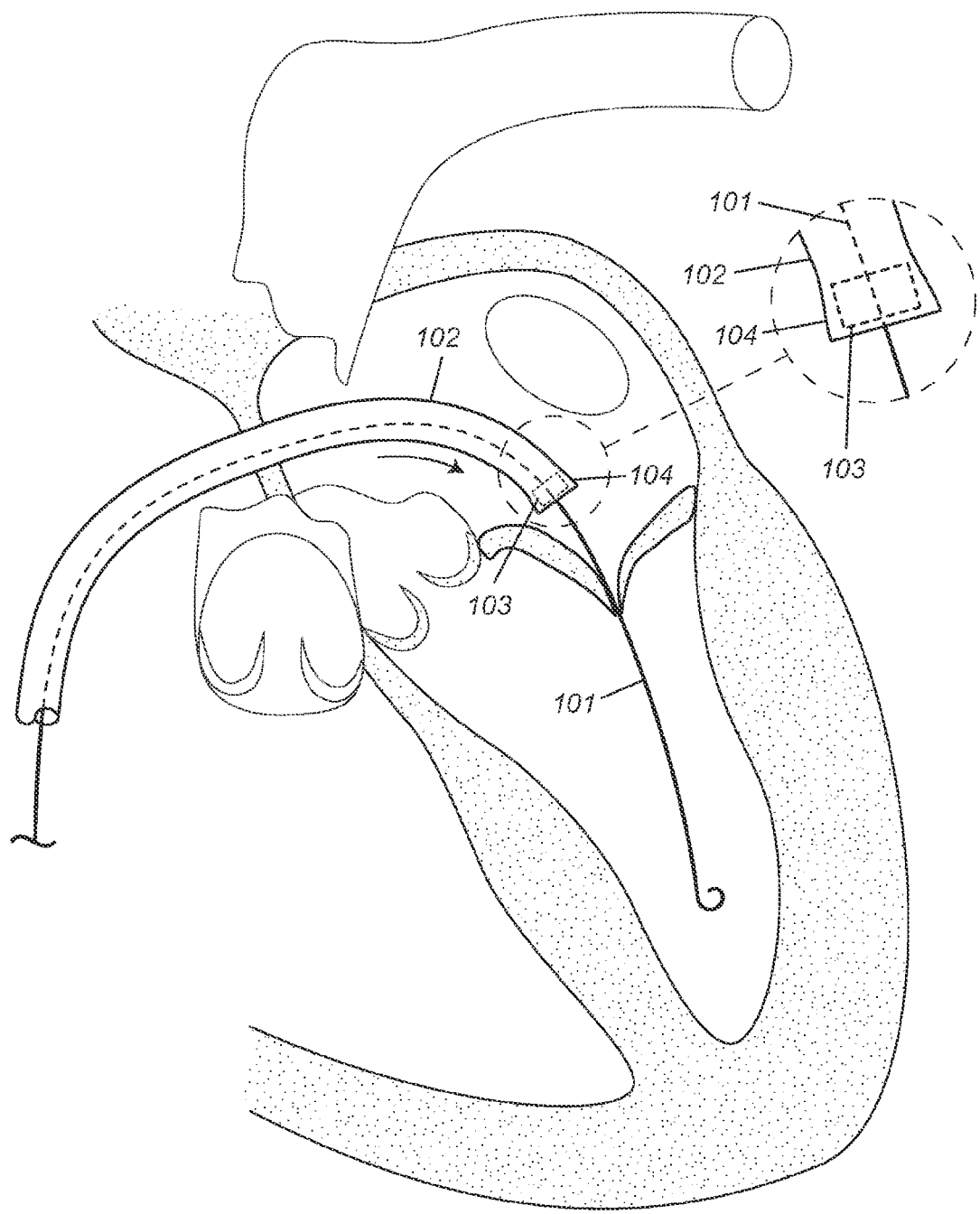
FIGS. 1C-D depict, in accordance with various embodiments of the present invention, a self-expandable DONUT device and a transseptal procedure of deploying the DONUT device to the mitral valve. 101 refers to a guide wire; 102 refers to a first delivery catheter; 103 refers to a self-expandable DONUT device; and 104 refers to an enclosing sheath at the first delivery catheter's distal end.
Figure 1D:
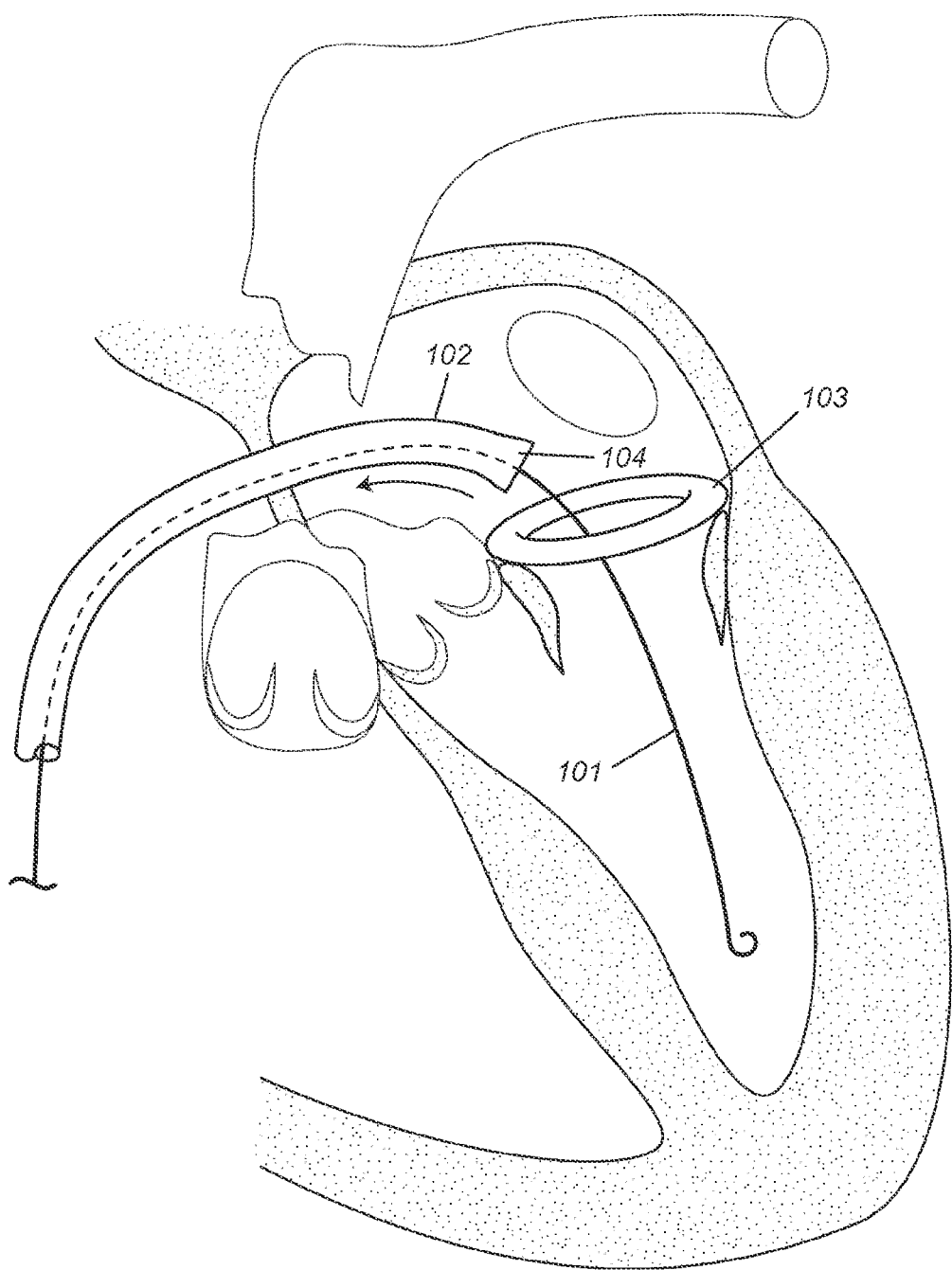

FIGS. 1C-1D illustrate an example of an implantation procedure for a DONUT device as disclosed herein. After induction of anesthesia, and sterile preparation, an incision is performed at the femoral vein. Alternatively, percutaneous femoral access may be performed with or without pre-closure. A guide wire 101 is inserted via the femoral vein and the right atrium, through a transseptal puncture on the inter-atrium septum, into the left atrium, thorough the mitral valve and into the left ventricle (FIG. 1C). A self-expandable DONUT device 103 is compressed and enclosed in the enclosing sheath 104 at the distal end of a first delivery catheter 102. The loaded first delivery catheter 102 is advanced over the guide wire 101 and inserted through the mitral valve into the left ventricle, and places the compressed DONUT device 103 on the atrial side of the mitral valve and near the valve annulus (FIG. 1C). The first delivery catheter 102 is retracted and the compressed DONUT device 103 is hence released out of the enclosing sheath 104 to expand (FIG. 1D). The expanded DONUT device's periphery conforms to the mitral valve's peri-annular anatomy and anchors to the atrial wall near the valve annulus (FIG. 1D).

Example 2 Balloon-Expandable DONUT

For Aortic Valve

Figure 2A:
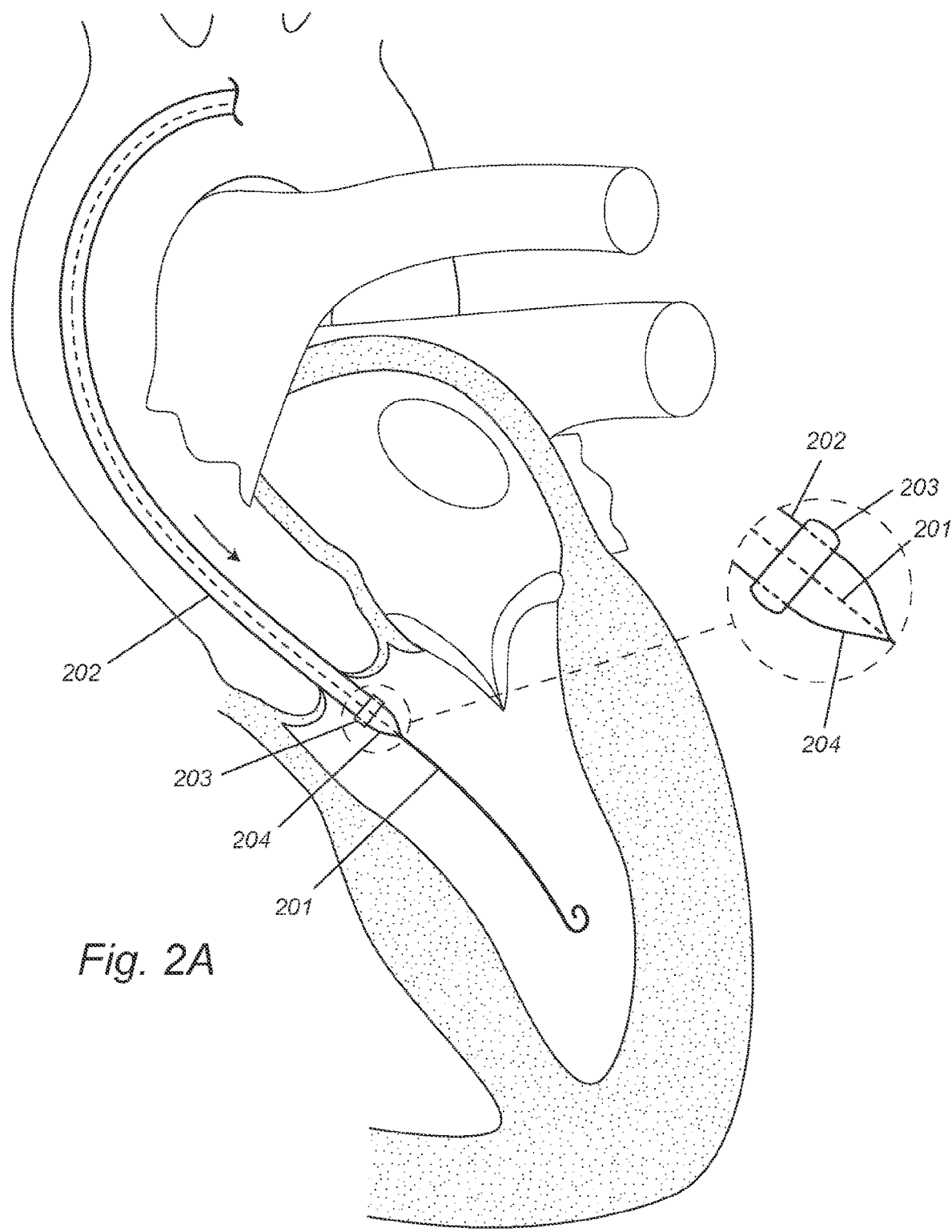
FIGS. 2A-C depict, in accordance with various embodiments of the present invention, a balloon-expandable DONUT device and a transfemoral procedure of deploying the DONUT device to the aortic valve. 201 refers to a guide wire; 202 refers to a first delivery catheter; 203 refers to a balloon-expandable DONUT device; and 204 refers to an inflatable balloon at the first delivery catheter's distal end.
Figure 2B:
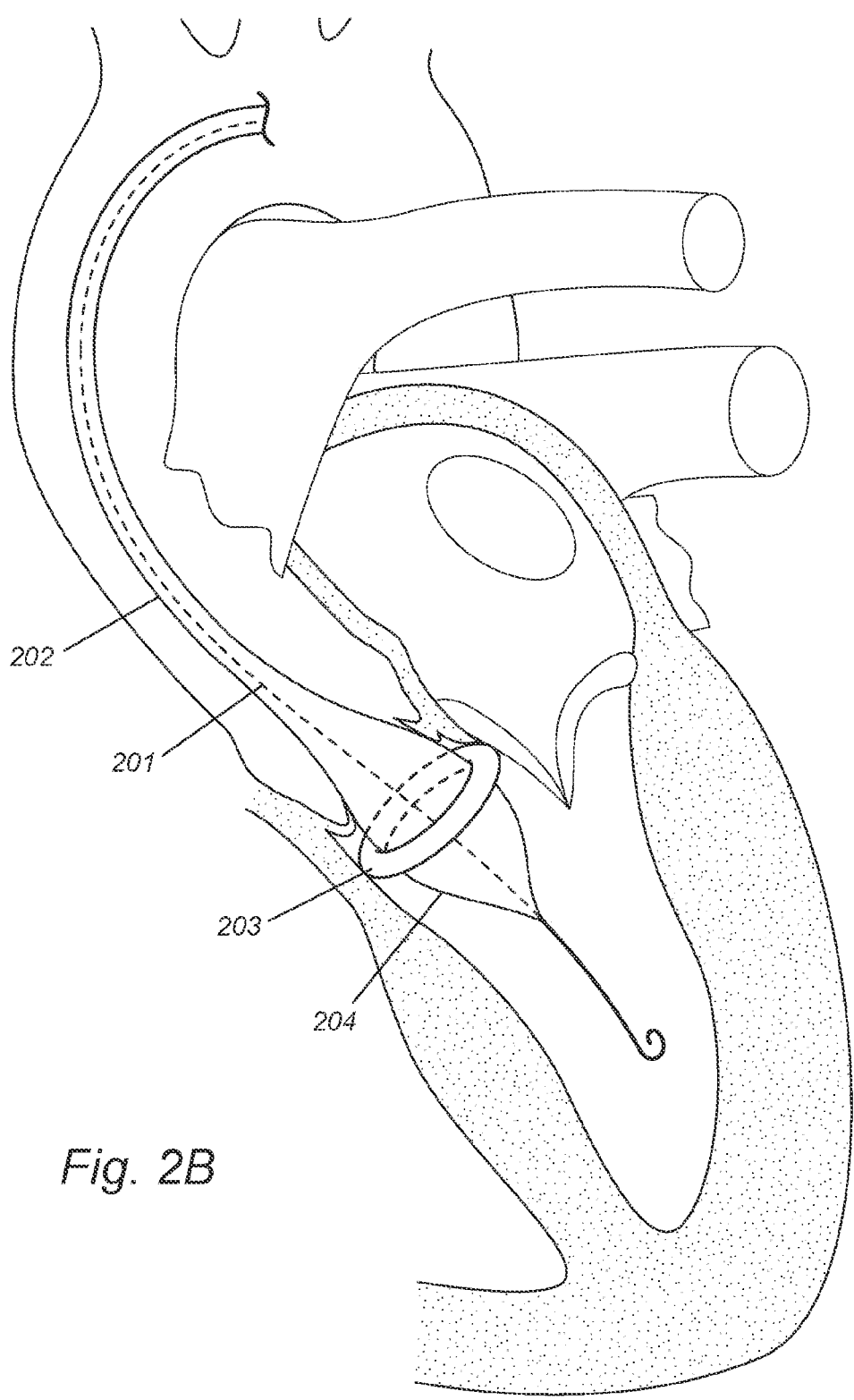
Figure 2C:
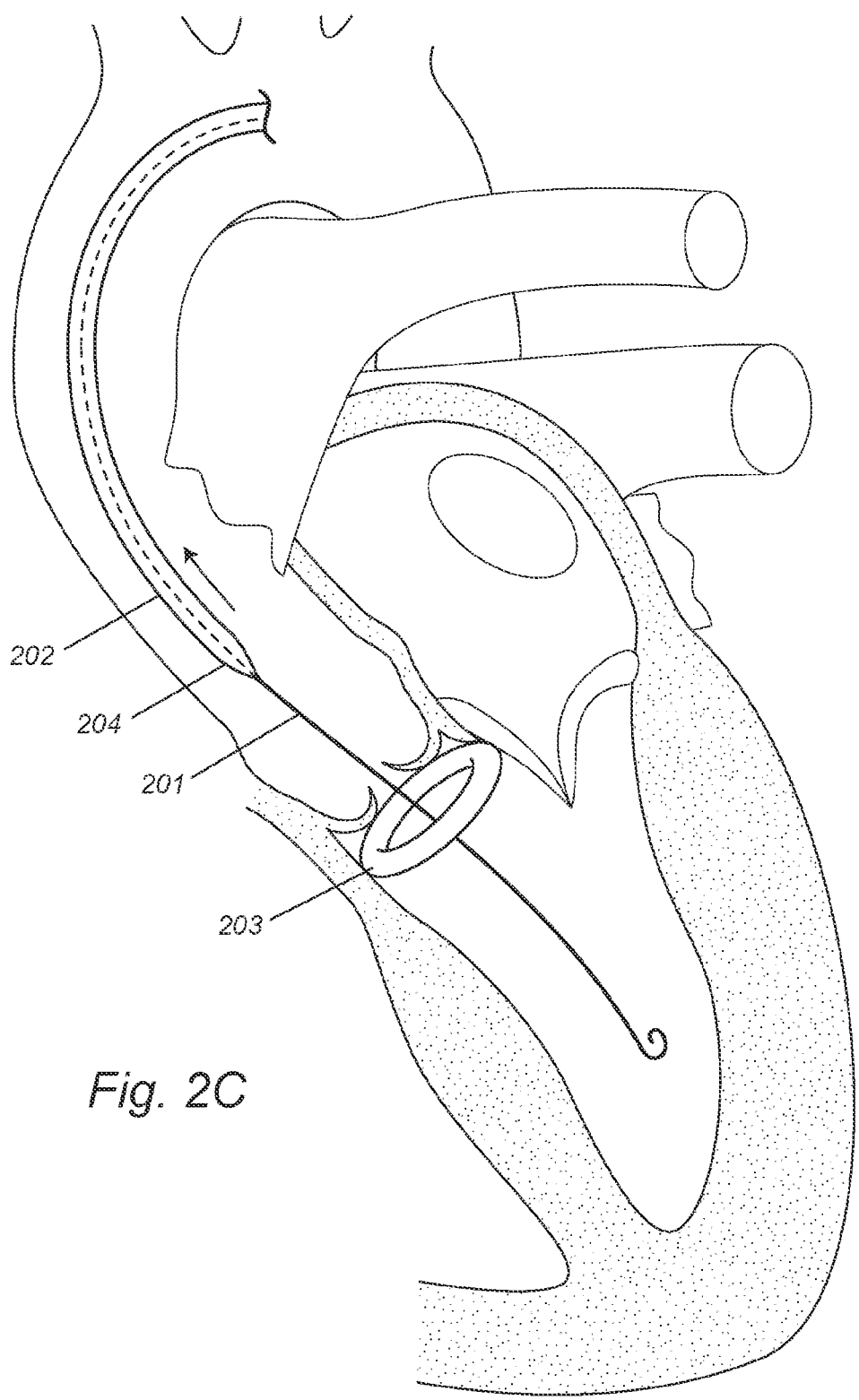

FIGS. 2A-2C illustrate an example of an implantation procedure for a DONUT device as disclosed herein. After induction of anesthesia, and sterile preparation, an incision is performed at the femoral artery. Alternatively, percutaneous femoral access may be performed with or without pre-closure. A guide wire 201 is inserted via the femoral artery and the ascending aorta through the aortic valve into the left ventricle (FIG. 2A). A balloon-expandable DONUT device 203 is compressed and mounted over the inflatable balloon 204 at the distal end of a first delivery catheter 202. The loaded first delivery catheter 202 is advanced over the guide wire 201 and inserted through the aortic valve into the left ventricle, and places the compressed DONUT device 203 on the ventricular side of the aortic valve and near the valve annulus (FIG. 2A). The inflatable balloon 204 is inflated to expand the compressed DONUT device 203 (FIG. 2B). The expanded DONUT device's periphery conforms to the aortic valve's peri-annular anatomy and anchors to the ventricular wall near the valve annulus (FIG. 2B). The inflatable balloon 204 is deflated and the first delivery catheter 202 is retracted (FIG. 2C).

For Mitral Valve

Figure 2D:
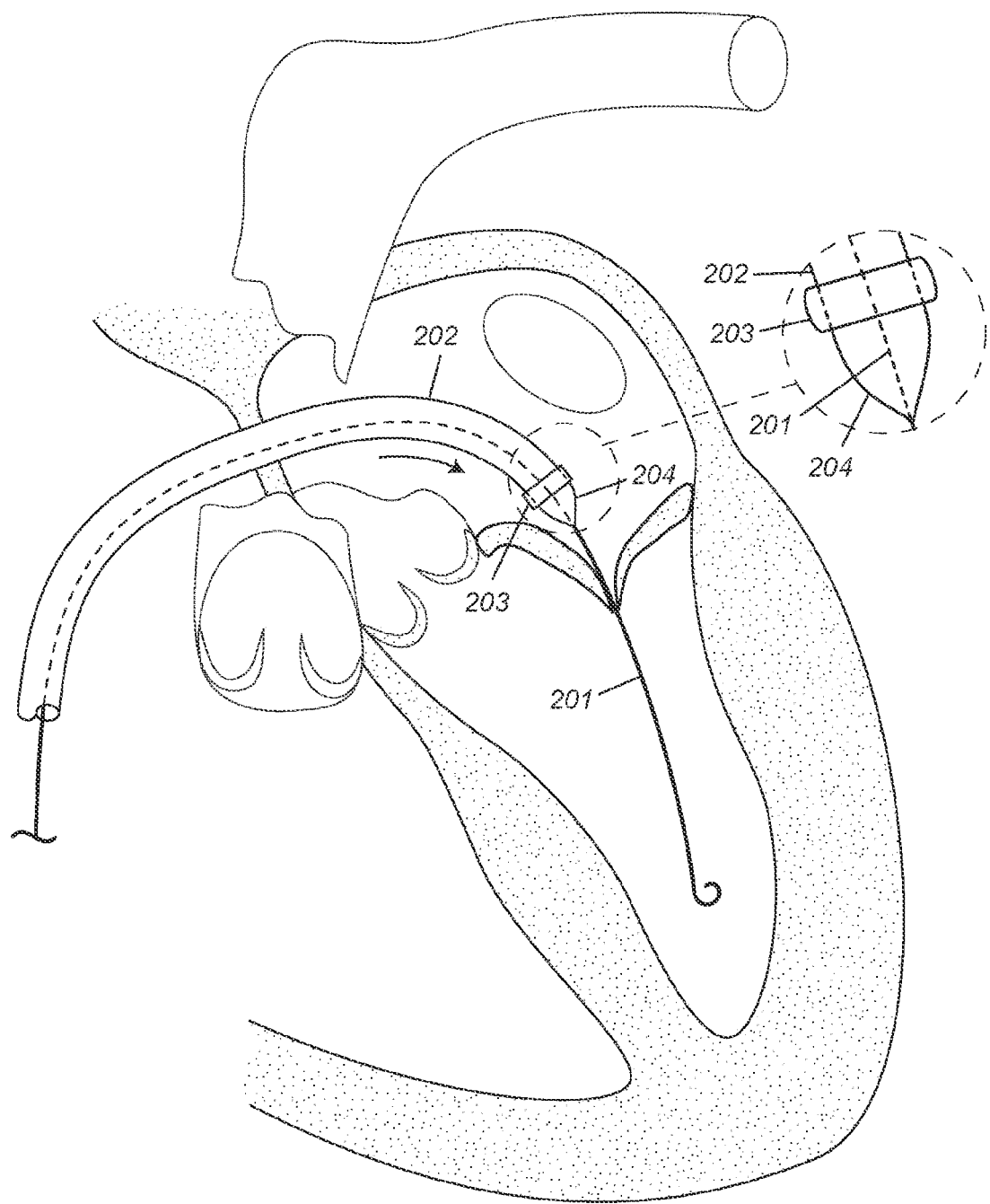
FIGS. 2D-F depict, in accordance with various embodiments of the present invention, a balloon-expandable DONUT device and a transseptal procedure of deploying the DONUT device to the mitral valve. 201 refers to a guide wire; 202 refers to a first delivery catheter; 203 refers to a balloon-expandable DONUT device; and 204 refers to an inflatable balloon at the first delivery catheter's distal end.
Figure 2E:
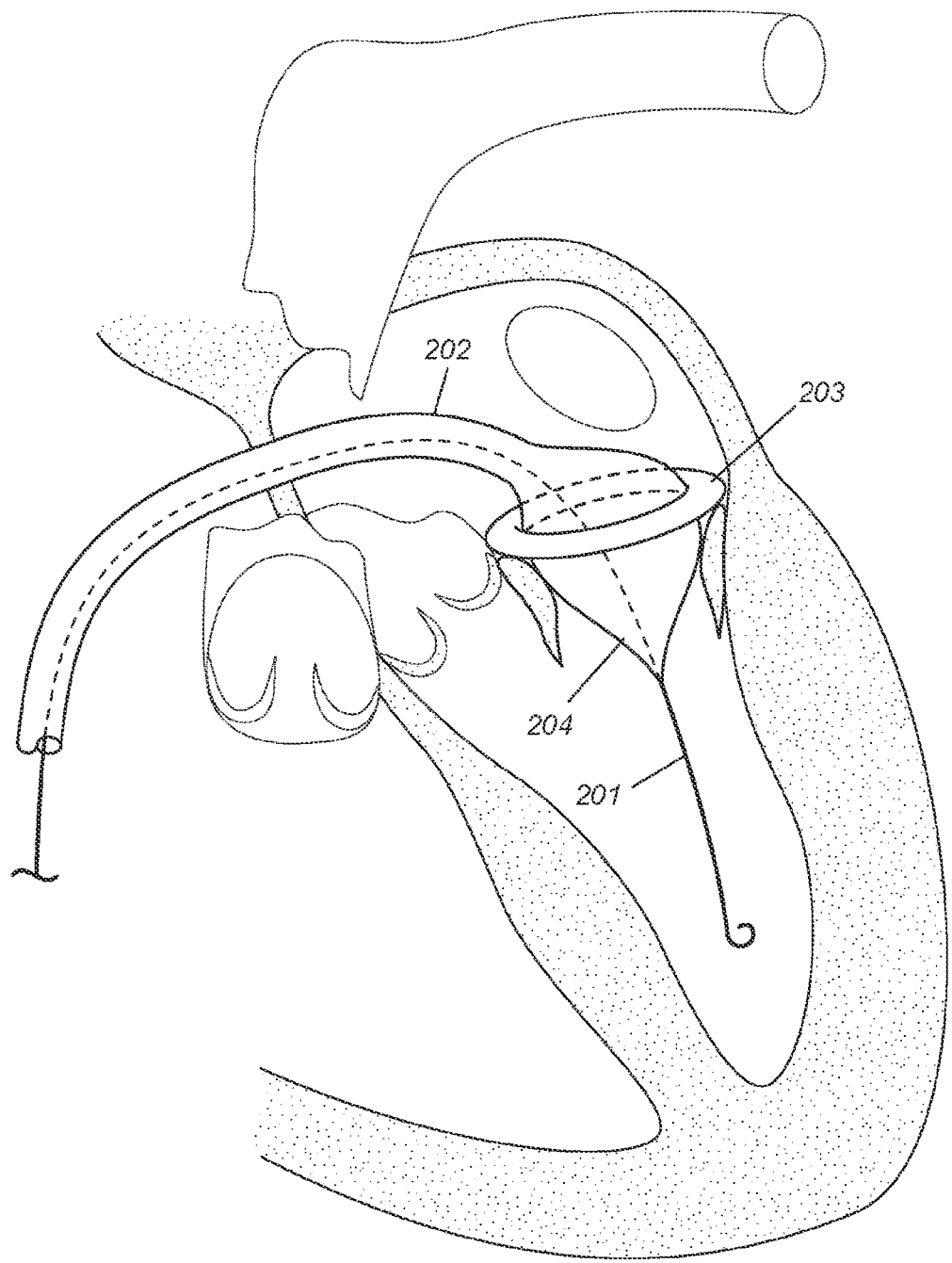
Figure 2F:
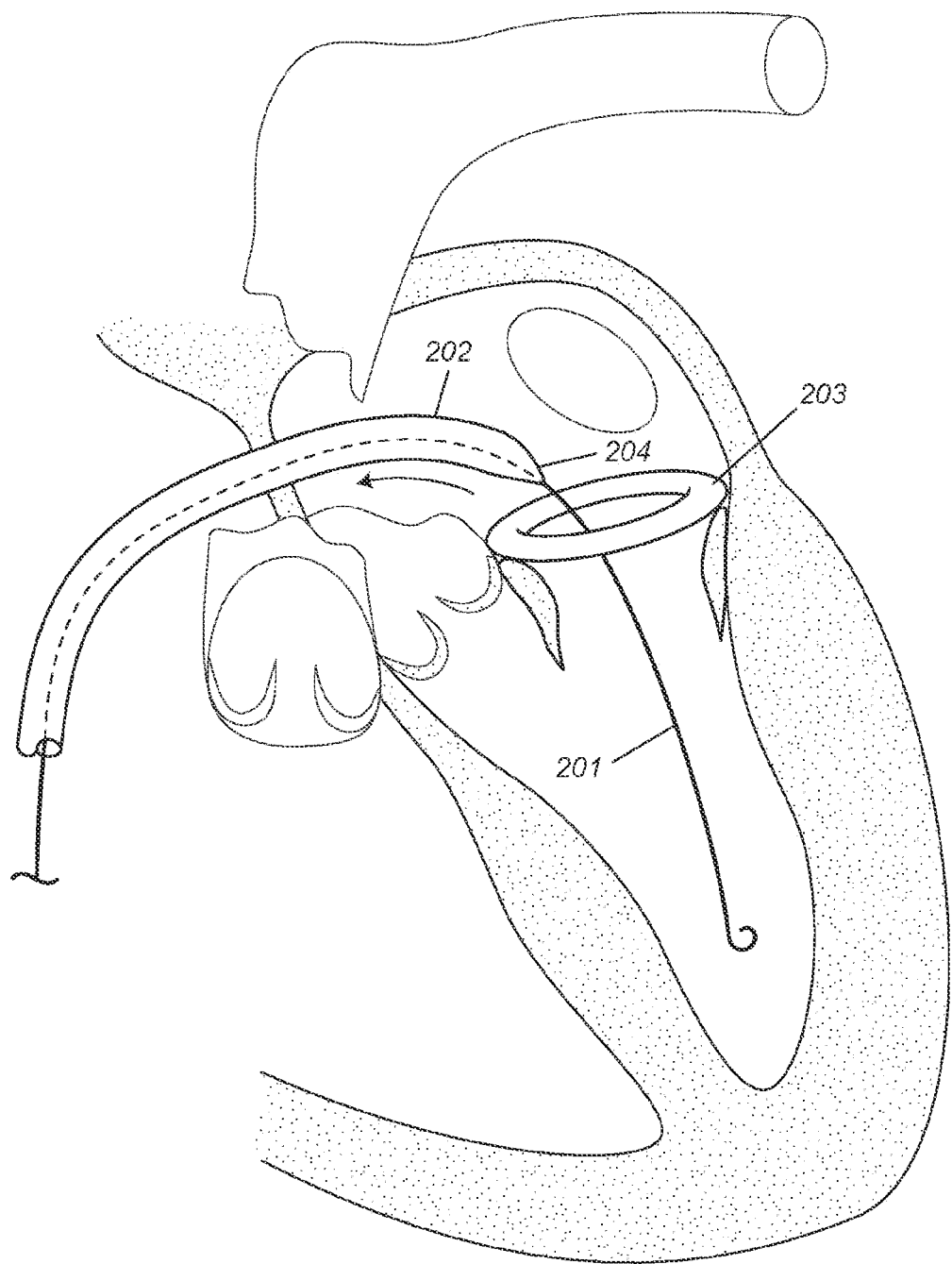

FIGS. 2D-1F illustrate an example of an implantation procedure for a DONUT device as disclosed herein. After induction of anesthesia, and sterile preparation, an incision is performed at the femoral vein. Alternatively, percutaneous femoral access may be performed with or without pre-closure. A guide wire 201 is inserted via the femoral vein and the right atrium, through a transseptal puncture on the inter-atrium septum, into the left atrium, thorough the mitral valve and into the left ventricle (FIG. 2D). A balloon-expandable DONUT device 203 is compressed and mounted over the inflatable balloon 204 at the distal end of a first delivery catheter 202. The loaded first delivery catheter 202 is advanced over the guide wire 201 and inserted through the mitral valve into the left ventricle, and places the compressed DONUT device 203 on the atrial side of the mitral valve and near the valve annulus (FIG. 2D). The inflatable balloon 204 is inflated to expand the compressed DONUT device 203 (FIG. 2E). The expanded DONUT device's periphery conforms to the mitral valve's peri-annular anatomy and anchors to the atrial wall near the valve annulus (FIG. 2E). The inflatable balloon 204 is deflated and the first delivery catheter 202 is retracted (FIG. 2F).

Example 3 Delivery of Self-Expandable Replacement Valve

Figure 3A:
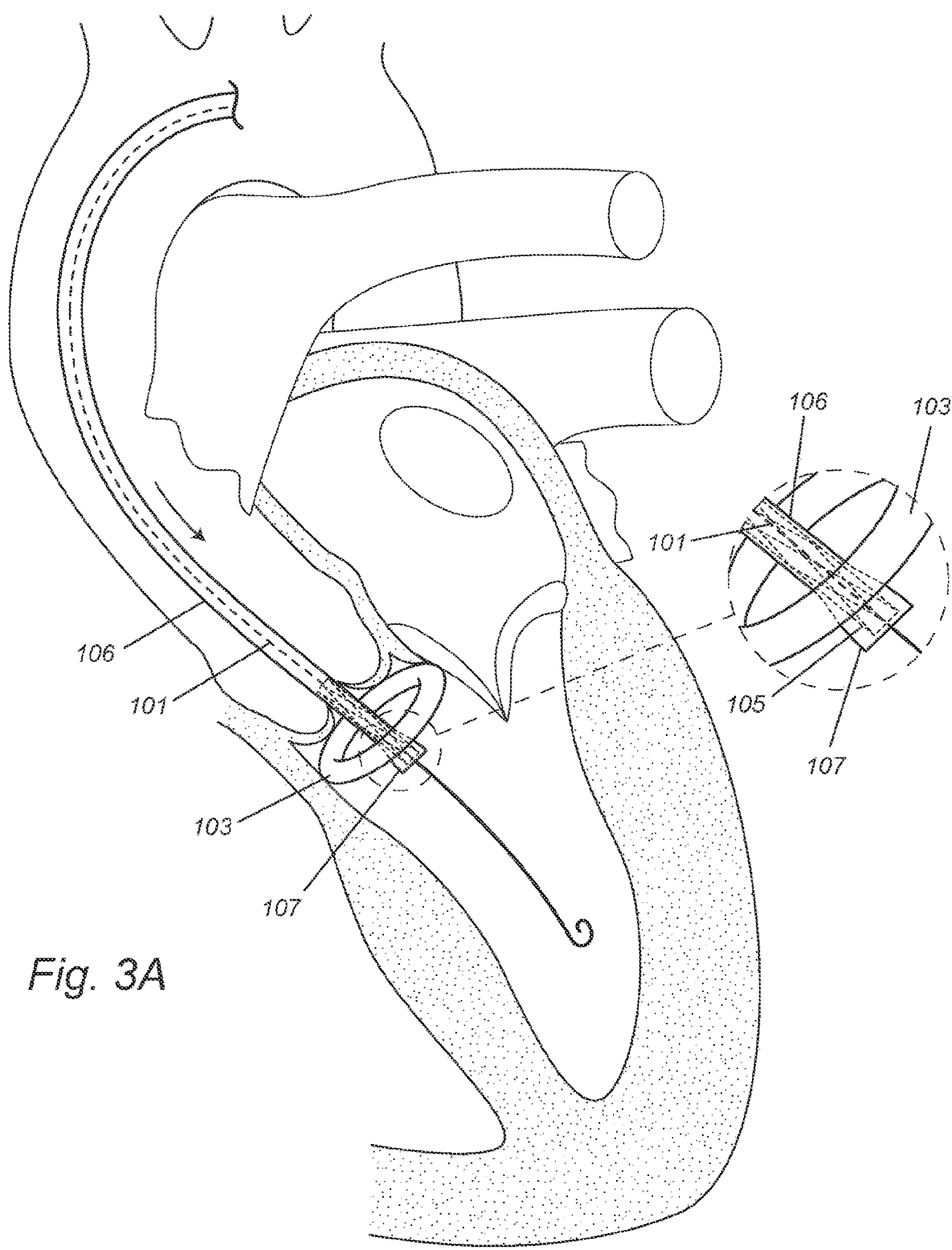
FIGS. 3A-B depict, in accordance with various embodiments of the present invention, a self-expandable replacement valve and a transfemoral procedure of deploying the replacement valve to the center hole of the DONUT device that is already deployed in the aortic valve. 101 refers to a guide wire; 103 refers to an already deployed DONUT device; 105 refers to a self-expandable replacement valve; 106 refers to a second delivery catheter; and 107 refers to an enclosing sheath at the second delivery catheter's distal end.
Figure 3B:
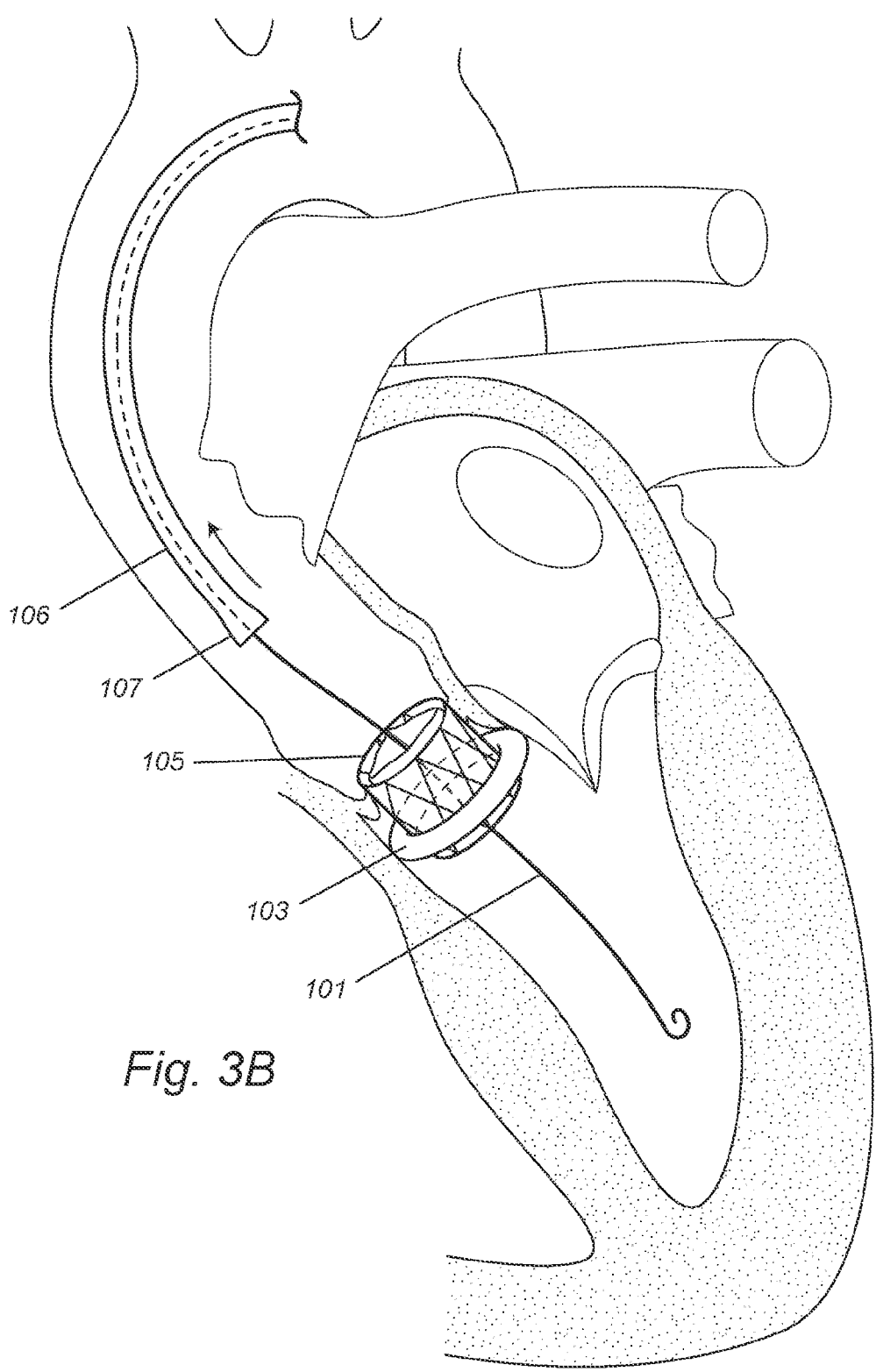

This is performed after the DONUT device is deployed to the aortic valve peri-annular region. A self-expandable replacement valve 105 is compressed and enclosed in the enclosing sheath 107 at the distal end of a second delivery catheter 106. The loaded second delivery catheter 106 is advanced over the guide wire 101 and inserted through the aortic valve into the left ventricle, and places the compressed replacement valve 105 across the aortic valve and the center hole of the DONUT device (FIG. 3A). The second delivery catheter 106 is retracted and the compressed replacement valve 105 is hence released out of the enclosing sheath 107 to expand (FIG. 3B). The expanded replacement valve anchors to the center hole of the DONUT device, thereby replacing the native aortic valve (FIG. 3B).

In various embodiments, the same or similar steps may be used for other heart valves, such as the mitral valve, pulmonary valve and tricuspid valve, in which cases the DONUT is first deployed to the respective heart valve peri-annular region. In various embodiments, the DONUT may be deployed in a cardiovascular structure or chamber distinct from the native valves to act as a platform for deployment of a transcatheter valve. This may include but is not restricted to the superior or inferior vena cava, the pulmonary artery or the ascending or descending aorta.

Additional standard steps that may be performed during the procedure include heparinization, and closure of the femoral artery or vein either by manual compression, suture-mediated pre-closure or surgical closure. The procedure may be performed by local anesthesia with conscious sedation or general anesthesia, in which case the patient is generally woken up immediately after the procedure. Heparinization may be reversed at the end of the procedure by administration of protamine. Heparin intolerant individuals may be anticoagulated during the procedure using direct thrombin inhibitors.

Example 4 Delivery of Balloon-Expandable Replacement Valve

Figure 4A:
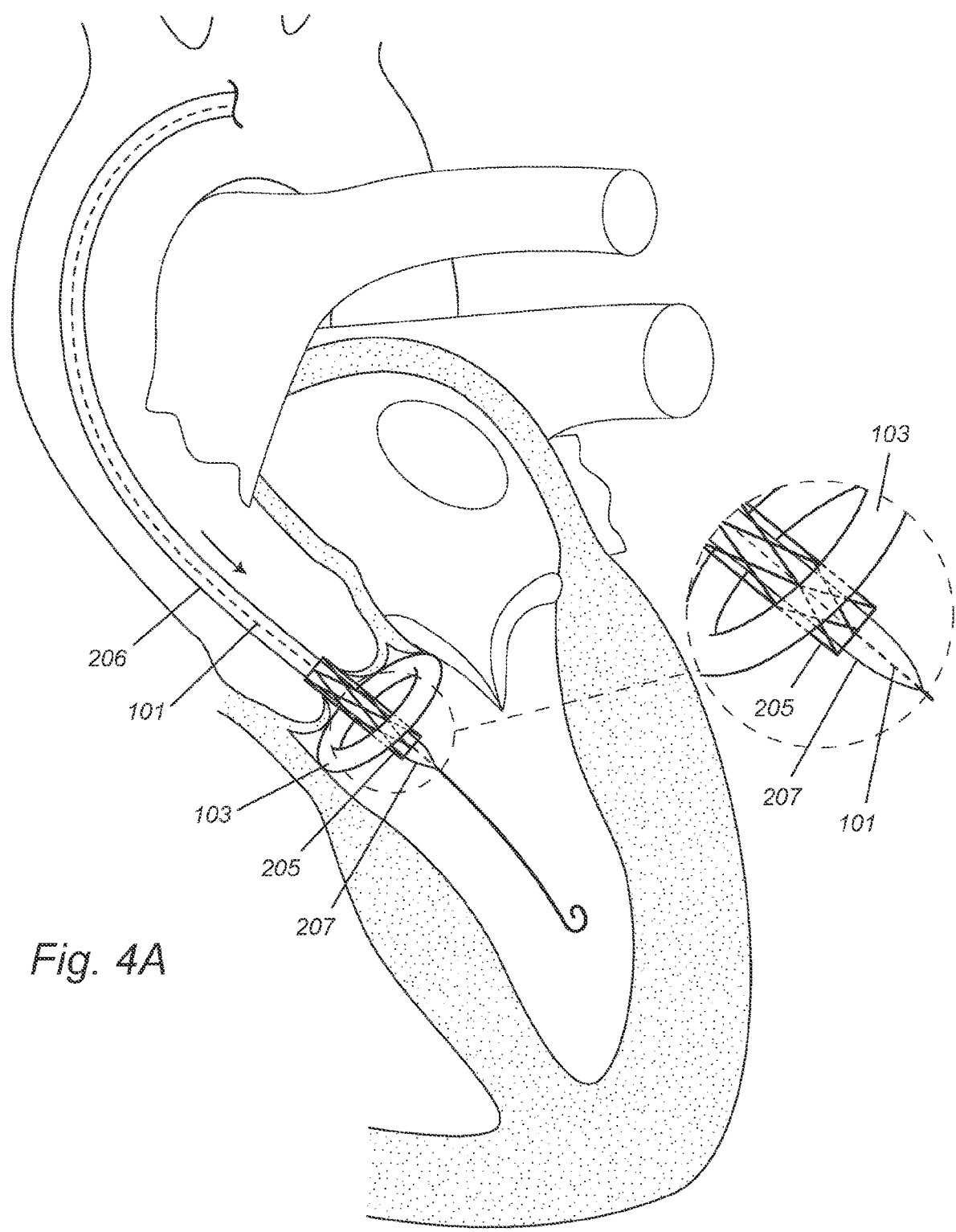
FIGS. 4A-C depict, in accordance with various embodiments of the present invention, a balloon-expandable replacement valve and a transfemoral procedure of deploying the replacement valve to the center hole of the DONUT device that is already deployed in the aortic valve. 101 refers to a guide wire; 103 refers to an already deployed DONUT device; 205 refers to a balloon-expandable replacement valve; 206 refers to a second delivery catheter; and 207 refers to an inflatable balloon at the first delivery catheter's distal end.
Figure 4B:
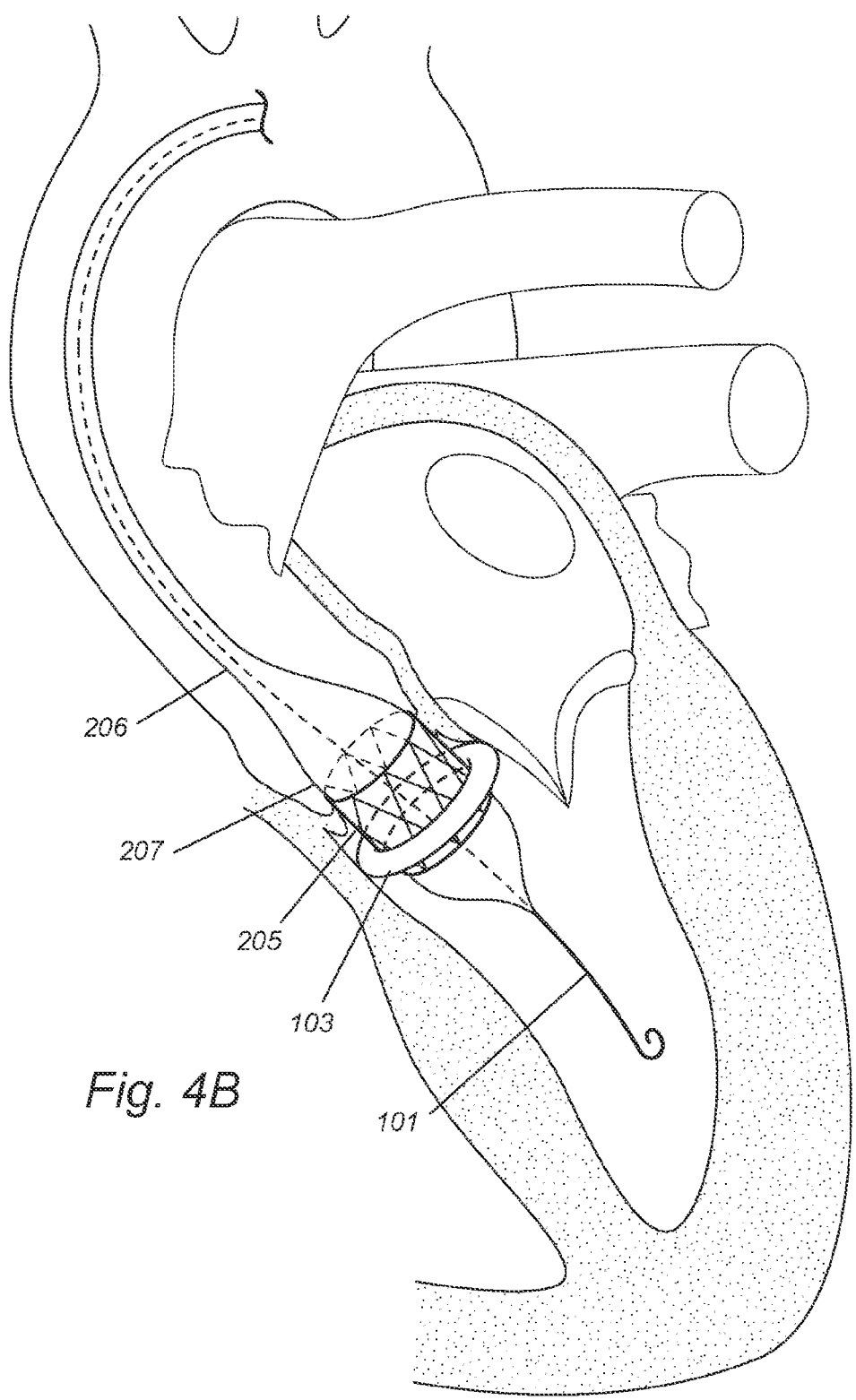
Figure 4C:
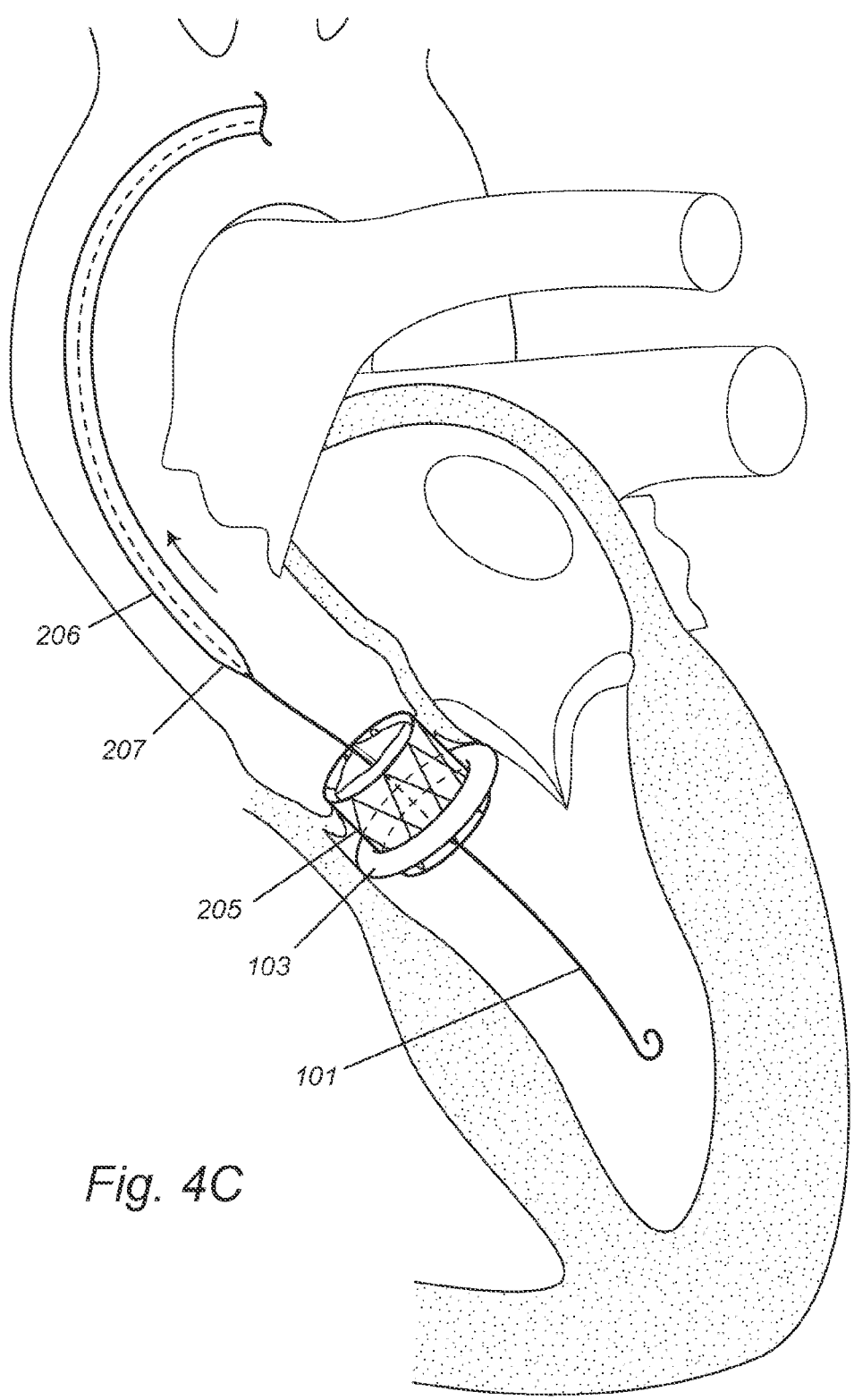
Figure 5A:
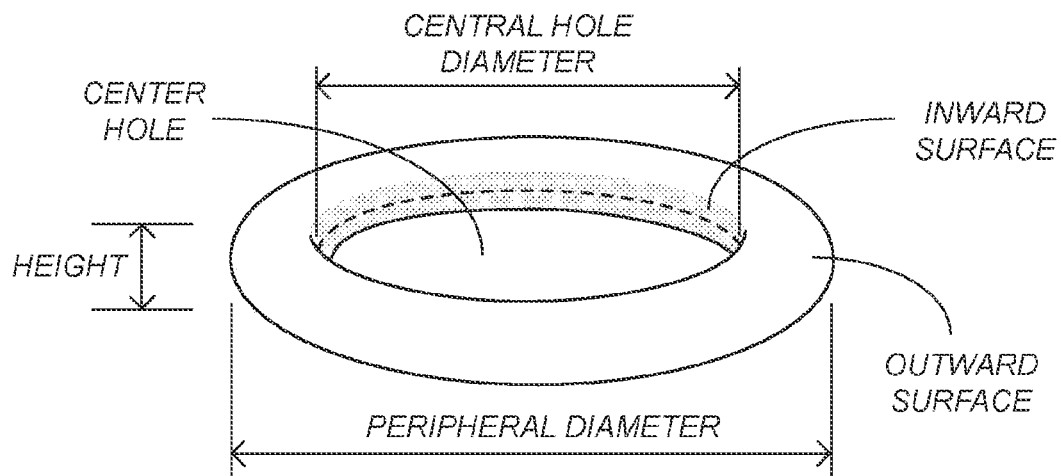
FIG. 5A shows that one non-limiting example of DONUT has an inward outside surface area (gray) that faces toward the center of the ring-shaped article and forms a center hole, and an outward outside surface area (white) that faces away from the center of the ring-shaped article and forms a periphery.
Figure 5B:
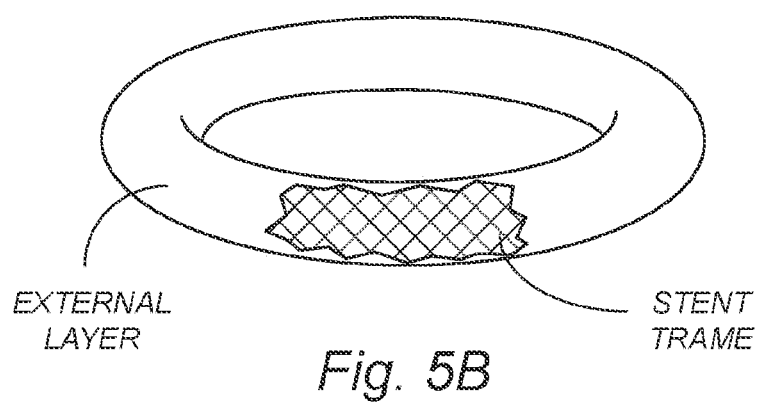
FIG. 5B shows that one non-limiting example of DONUT has a stent frame covered with an external layer. After the DONUT device is anchored to a native heart valve peri-annular region, a replacement heart valve is anchored in its center hole to replace (or rather, implant within) the native heart valve.

This is performed after the DONUT device is deployed to the aortic valve peri-annular region. A balloon-expandable replacement valve 205 is compressed and mounted over the inflatable balloon 207 at the distal end of a second delivery catheter 206. The loaded second delivery catheter 206 is advanced over the guide wire 101 and inserted through the aortic valve into the left ventricle, and places the compressed replacement valve 205 across the aortic valve and the center hole of the DONUT device (FIG. 4A). The inflatable balloon 207 is inflated to expand the compressed DONUT device 205 (FIG. 4B). The expanded replacement valve 205 anchors to the center hole of the DONUT device, thereby replacing the native aortic valve (FIG. 4B). The inflatable balloon 207 is deflated and the second delivery catheter 206 is retracted (FIG. 4C).

In various embodiments, the same or similar steps may be used for other heart valves, such as the mitral valve, pulmonary valve and tricuspid valve, in which cases the DONUT is first deployed to the respective heart valve.

Additional standard steps that may be performed during the procedure include heparinization, and closure of the femoral artery or femoral vein either by manual compression, suture-mediated pre-closure or surgical closure. The procedure may be performed by local anesthesia with conscious sedation or general anesthesia, in which case the patient is generally woken up immediately after the procedure. Heparinization may be reversed at the end of the procedure by administration of protamine. Heparin intolerant individuals may be anticoagulated during the procedure using direct thrombin inhibitors.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A device configured to receive a self-expandable or balloon-expandable replacement heart valve for transcatheter valve replacement, comprising:
a ring-shaped article comprising a stent frame, the entire exterior surface of the stent frame being covered with a hollow external layer,
wherein the ring-shaped article comprises an outside surface corresponding to an outside surface of the hollow external layer,
wherein the outside surface comprises an inward surface area that faces toward the center of the ring-shaped article and forms a center hole,
wherein the outside surface comprises an outward surface area that faces away from the center hole of the ring-shaped article and forms a periphery,
wherein the ring-shaped article has a compressed status and an expanded status,
wherein when the ring-shaped article is expanded, the center hole is configured to fit and receive a replacement heart valve configured to anchor to the center hole of the ring-shaped article, and the periphery is configured to mould to a native anatomy of a heart valve peri-annular region, cardiovascular structure or chamber, and
wherein the ring-shaped article's height is configured to be less than a replacement heart valve's height.

2. The device of claim 1, wherein the heart valve is a mitral, aortic, tricuspid or pulmonary valve.

3. The device of claim 1, wherein the periphery is configured to anchor to the heart valve peri-annular region or the periphery is configured to anchor to the ventricular, atrial, aortic, or arterial wall.

4. The device of claim 1, wherein the ring-shaped article is configured to receive the replacement heart valve deployed to the center hole of the ring-shaped article after the ring-shaped article is deployed and anchored to the native heart valve peri-annular region.

5. The device of claim 1, wherein the ring-shaped article is configured to be are not connected to a replacement heart valve before, during or after deployment of the ring-shaped article and the replacement heart valve.

6. The device of claim 1, wherein,
the replacement heart valve is about 10-55 mm in height;
the ring-shaped article is about 5-55 mm in height;
the replacement heart valve is about 10-55 mm in diameter;
the center hole of the ring-shaped article is about 10-55 mm in diameter; and
the periphery of the ring-shaped article is about 15-80 mm in diameter.

7. The device of claim 1, wherein the center hole of the ring-shaped article is shaped as circular, elliptical, oval, or a D ring to match a shape of the replacement heart valve, and the periphery of the ring-shaped article is shaped to conform to the region in which the device is deployed.

8. The device of claim 7, wherein the cross section of the replacement heart valve is a circle, ellipse, oval, or D-shape.

9. The device of claim 1, wherein the ring-shaped article is configured to receive a replacement heart valve separately delivered and/or deployed to the native anatomy of the heart valve peri-annular region.

10. The device of claim 1, wherein the stent frame is made of iron, platinum, titanium, nickel, chromium, cobalt, magnesium, stainless steel, nitinol (nickel-titanium), nickel-chromium, cobalt-chromium, or platinum-iridium, or a combination thereof.

11. The device of claim 1, wherein the ring-shaped article is self-expandable or balloon-expandable and is configured to receive an expanded replacement heart valve anchored to the center hole of the ring-shaped article.

12. The device of claim 1, wherein the replacement heart valve comprises a stent frame made of iron, platinum, titanium, nickel, chromium, cobalt, magnesium, stainless steel, nitinol (nickel-titanium), nickel-chromium, cobalt-chromium, or platinum-iridium, or a combination thereof, or of a solid or hollow plastic material.

13. The device of claim 1, wherein the replacement heart valve is a prosthetic valve or a bioprosthetic valve.

14. The device of claim 1, wherein the replacement heart valve comprises one, two, three, or more leaflets.

15. The device of claim 1, wherein the hollow external layer is inflatable and/or self-expandable.

16. The device of claim 1, wherein the ring-shaped article is configured to be deployed by a first delivery catheter into the heart valve peri-annular region.

17. The device of claim 16, wherein the first delivery catheter comprises an inflatable balloon near or at its distal end, wherein the ring-shaped article is configured to be mounted on the inflatable balloon when compressed, and wherein the inflatable balloon is configured to be inflated so as to expand the ring-shaped article when compressed.

18. The device of claim 16, wherein the first delivery catheter comprises an enclosing sheath near or at its distal end, wherein the ring-shaped article is configured to be enclosed in the enclosing sheath when compressed, and wherein the enclosing sheath is configured to be retracted so as to expand the ring-shaped article.

19. The device of claim 16, wherein the first delivery catheter is configured to be inserted over a guide wire.

20. The device of claim 16, wherein the center hole of the ring-shaped article is configured to receive a replacement heart valve deployed by a second delivery catheter, the second delivery catheter being different from the first delivery catheter.

21. The device of claim 20, wherein the second delivery catheter is configured to be inserted over a guide wire.

22. The device of claim 1, wherein the ring-shaped article's height is about 5-10%, 10-20%, 20-30%, 30-40%, 40-50%, 50-60%, 60-70%, 70-80%, 80-90%, or 90-95% of the replacement heart valve's height.

23. The device of claim 22, wherein the ring-shaped article's height is about 20-30%, 30-40%, 40-50%, or 50-60% of the replacement valve's height.

24. A system for transcatheter valve replacement, the system comprising:
a ring-shaped article comprising a hollow fabric and/or plastic material inflatable with air, fluid, or a plastic resin,
wherein the ring-shaped article comprises an outside surface,
wherein the outside surface comprises an inward surface area that faces toward the center of the ring-shaped article and forms a center hole,
wherein the outside surface comprises an outward surface area that faces away from the center hole of the ring-shaped article and forms a periphery,
wherein the ring-shaped article has a compressed status and an expanded status, and
wherein when the ring-shaped article is expanded, the center hole is configured to fit and receive a replacement heart valve, and the periphery is configured to mould to a native anatomy of a heart valve peri-annular region, cardiovascular structure or chamber;

a first delivery catheter configured to deploy the ring-shaped article into the heart valve peri-annular region; and a second delivery catheter configured to deploy the replacement heart valve into the center hole of the ring-shaped article.

\* \* \* \* \*